United States Patent
Ntziachristos et al.

(10) Patent No.: US 8,314,406 B2
(45) Date of Patent: Nov. 20, 2012

(54) SYSTEMS AND METHODS FOR OPTICAL IMAGING USING EARLY ARRIVING PHOTONS

(75) Inventors: Vasilis Ntziachristos, Larissa (GR); Mark J. Niedre, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 327 days.

(21) Appl. No.: 12/594,351

(22) PCT Filed: Apr. 4, 2008

(86) PCT No.: PCT/US2008/059369
§ 371 (c)(1),
(2), (4) Date: Oct. 2, 2009

(87) PCT Pub. No.: WO2009/009178
PCT Pub. Date: Jan. 15, 2009

(65) Prior Publication Data
US 2010/0078576 A1    Apr. 1, 2010

Related U.S. Application Data

(60) Provisional application No. 60/910,520, filed on Apr. 6, 2007.

(51) Int. Cl.
*G01N 21/64* (2006.01)
(52) U.S. Cl. .................................. 250/458.1
(58) Field of Classification Search ............... 250/458.1
See application file for complete search history.

(56) References Cited

U.S. PATENT DOCUMENTS

| 5,148,031 A  * | 9/1992 | Kamalov et al. ........... 250/458.1 |
| 5,919,140 A | 7/1999 | Perelman et al. |
| 6,070,583 A | 6/2000 | Perelman et al. |
| 6,321,111 B1 | 11/2001 | Perelman et al. |
| 6,930,314 B2 * | 8/2005 | Jackson et al. ............. 250/458.1 |

FOREIGN PATENT DOCUMENTS

| WO | WO 2005/089637 A2 | 9/2005 |
| WO | WO 2005/089637 A3 | 9/2005 |

OTHER PUBLICATIONS

PCT International Preliminary Report on Patentability and Written Opinion dated Oct. 15, 2009 for PCT/US2008/059369 filed on Apr. 4, 2008.

Ntziachristos et al.; "Early Photon Optical Tomography;" 2005 International Conference on Acoustics, Speech, and Signal Processing; vol. 5; ISBN: 0-7803-8874-7; pp. V-837 to V-840.

Turner et al.; "Complete-angle projection diffuse optical tomography by use of early photons;" Optics Letters; vol. 30, No. 4; Feb. 15, 2005; pp. 409-411.

(Continued)

*Primary Examiner* — Constantine Hannaher
(74) *Attorney, Agent, or Firm* — Daly, Crowley, Mofford & Durkee, LLP

(57) ABSTRACT

Optical imaging systems and methods use early photons in order to generate processed fluorescent light images of fluorescent material on or within a tissue. The early photons are generated in accordance with a pulsed light source and an early-photon light receiver. The processed fluorescent light images tend to have improved resolution and imaging accuracy compared with fluorescent light images generated with photons beyond the early photons portions.

64 Claims, 8 Drawing Sheets

OTHER PUBLICATIONS

Turner et al.; "Inversion with early photons;" Medical Physics; vol. 34, No. 4; Mar. 21, 2007; pp. 1405-1411.
PCT Search Report and Written Opinion of the ISA for PCT/US2008/059369 dated Mar. 23, 2009.

Chen et al.: "Optical Computed Tomography in a Turbid Medium Using Early Arriving Photons;" Journal of Biomedical Optics; vol. 5, No. 2; Apr. 2000; pp. 144-154.

* cited by examiner

SYSTEMS AND METHODS FOR OPTICAL IMAGING USING EARLY ARRIVING PHOTONS

CROSS REFERENCE TO RELATED APPLICATIONS

This application is a U.S. National Stage application of International Patent Application PCT/US2008/059369 filed Apr. 4, 2008, published in the English language as WO 2009/009178 on Jan. 15, 2009, which claims the benefit of U.S. Provisional Patent Application No. 60/910,520 filed on Apr. 6, 2007.

STATEMENT REGARDING FEDERALLY SPONSORED RESEARCH

This invention was made with Government support under Grant No.(s) EB000750 awarded by the National Institutes of Health. The Government has certain rights in this invention.

FIELD OF THE INVENTION

This invention relates generally to optical imaging systems and methods and, more particularly, to optical imaging systems and methods that detect early-arriving photons emitted by a fluorescent material within a heterogeneous specimen (e.g., a mammal) and provide an image of the fluorescent material in which the effect of inhomogeneity of light propagation within the specimen is reduced.

BACKGROUND OF THE INVENTION

Fluorescent light images can be generated in-vivo for imaging of physiological and molecular functions and gene expression in live biological tissues. Fluorescence imaging of small animals has been used in biological research, including research in drug discovery and in understanding disease and normal development. Fluorescence imaging has also been used to study various human tissues, for example, tissues exhibiting epithelial diseases, the human breast, joints, and human teeth.

Conventionally, fluorescent light has been used to generate images of histological slices of biological tissue using so-called fluorescence microscopy. Fluorescence microscopy is used to provide relatively high-resolution images. However, tissue sectioning used in conventional fluorescence microscopy is limited to slice thicknesses (i.e., tissue depths) on the order of half a millimeter, and therefore, conventional fluorescence microscopy is not appropriate for imaging through entire organs or through the whole body of an animal or human.

In order to provide images deeper into tissue, conventional systems and techniques have used illumination light sources that can excite near infrared (NIR) fluorescent light from fluorochromes within the tissue. The near infrared light is selected because near infrared light is only mildly absorbed by tissue (compared to visible light) and can propagate several centimeters through biological tissue. Near infrared light is used in a variety of optical imaging systems and techniques.

The most common macroscopic technique that is conventionally used for fluorescence imaging is fluorescence reflectance imaging (FRI), which is also referred to herein as fluorescence epi-illumination imaging (FEI). Epi-illumination light sources and epi-illumination imaging are further described below. In general, an epi-illumination light source generates epi-illumination light that is directed toward a surface of biological tissue. The epi-illumination light propagates upon or into the biological tissue and excites fluorescent light from fluorescent material on or within the biological tissue. To form a fluorescent epi-illumination image, the fluorescent light is collected generally on the same side of the tissue as the epi-illumination light source.

As described above, an FEI system transmits light onto and/or into biological tissue and collects the fluorescent light that is emitted back from within the tissue. In some arrangements, the emitted light is near infrared light. The emitted light can be visually inspected or it can be captured with a CCD camera or other photon detector positioned generally on the same side of the tissue as the epi-illumination light source.

A second method, which has not yet been fully utilized for research using small animals, but which has found applications in optical breast imaging, uses a transillumination light source to generate transillumination images. Similar to the above-described epi-illumination light source, a transillumination light source generates transillumination light that propagates into the tissue and excites fluorescent light from a fluorescent material on or within the biological tissue. However, unlike epi-illumination light, the transillumination light propagates entirely through the tissue. In transillumination imaging, fluorescent light is collected generally on the opposite side of the tissue from the transillumination light source.

Similar to that described above for fluorescence epi-illumination imaging, in fluorescence trans-illumination imaging, excitation light (for example, near-infrared light) from a trans-illumination light source is used to illuminate the tissue. The trans-illumination light source is used to excite fluorescent material within the tissue that, in turn, emits fluorescent light. However, in contrast to the above-described fluorescence epi-illumination arrangement, in fluorescence transillumination imaging, a CCD camera or other photon detector is positioned generally on the opposite side of the tissue from the transillumination light source. In some arrangements, the emitted light is near infrared light. Fluorescence transillumination imaging (FTI) has been used to visualize functional characteristics of cardiac muscle and in dental diagnostic practice.

In some transillumination arrangements, the transillumination light source and the light detector lie on a virtual line passing through the tissue. In some arrangements the virtual line is generally perpendicular to the tissue and, in other arrangements, the virtual line is not generally perpendicular to the tissue.

Fluorescence epi-illumination imaging (FEI) and fluorescence transillumination imaging (FTI) can result in "planar" images, which are two-dimensional images.

More advanced optical imaging systems and methods have been developed, which utilize tomographic techniques. These systems and methods operate by obtaining photonic measurements at different projections (i.e., angles or slices) to the tissue and combining the measurements using a tomographic algorithm. Tomography can provide a more accurate image than the above-described forms of planar imaging. Advantages of tomography include a superior ability for image quantification, an ability to provide two-dimensional or three-dimensional images, an ability to provide three-dimensional imaging with feature depth measurements, and higher sensitivity and higher resolution as compared to planar imaging, especially deeper in tissue. In some applications, tomography has been used in-vivo to measure enzyme up-regulation and treatment response to drugs. In these applications, tomography provides superior imaging performance compared to planar imaging. However, tomography is more complex than planar imaging, requiring more advanced instrumentation, requiring multiple illumination points (projections), which can require multiple light sources, and requiring advanced theoretical methods for modeling photon propagation in tissues.

A common assumption in conventional NIR optical tomography is that propagation in a diffuse medium has high scattering but relatively low absorption, as provided by the NIR window. This assumption has allowed derivation of a "diffusion equation" associated with a "transport equation," by means of a "diffusion approximation," which provides an effective tool for modeling NIR photon propagation in tissues. The transport equation is described, for example, in K. M. Case and P. F. Zweifel, "Linear Transport Theory," Addison-Wesley, MA, (1967) and the diffusion approximation in K. Furutsu and Y. Yamada, "Diffusion Approximation for a Dissipative Random Medium and the Applications," Phys. Rev. E 50, 3634 (1994).

While optical imaging associated with fluorochromes is described above, fluorescent proteins are also known materials that can be formed within biological tissue, and which can be excited by excitation light in order to emit fluorescent light from within a biological tissue. However, as is known, all currently available fluorescent proteins utilize excitation light having a wavelength in the visible range. Moreover, conventional fluorescent proteins emit visible fluorescent light when excited. Tomographic imaging using visible light, as provided by the conventional fluorescent proteins, is complicated by a relatively high absorption of visible light propagating in biological tissue, which results in significant attenuation.

Other, more advanced solutions (other than the above-described diffusion approximation) to the transport equation have been generated and applied to NIR optical tomography. The advanced solutions overcome inadequacies of the above-mentioned diffusion approximation. However the advanced solutions to the transport equation are generally computationally expensive and become impractical for tomographic systems having a large number of excitation light sources, resulting in large data sets.

In order to provide a plurality of images necessary for tomography, many conventional optical tomography systems use an optical switch as part of a light source assembly in order to use a single light element to project at a variety of angles or positions relative to a specimen. It is known that the optical switch generates energy losses.

SUMMARY OF THE INVENTION

The systems and methods of the present invention provide an improved fluorescent light image representative of a spatial distribution (e.g., concentration) of fluorescent material (e.g., a fluorescent probe) disposed in or on a biological tissue. The fluorescent light image may be, for example, a tomographic image or a planar image. The systems and methods generate the images by detecting early-arriving photons, rather than all photons, associated with a particular illumination light pulse.

In one aspect, the invention provides a system for optical imaging including a light source configured to project illumination light including one or more illumination light pulses into a specimen having a fluorescent material therein (e.g., fluorescent probe or endogenous material). The illumination light includes excitation light that becomes intrinsic light within the specimen and excites the fluorescent material within the specimen, thereby producing fluorescent light. At least a portion of the fluorescent light and the intrinsic light exit the specimen. The system also includes an early-photon light detector configured to detect one or more fluorescent light early photon portions associated with the exiting fluorescent light, as well as one or more intrinsic light early photon portions associated with the exiting intrinsic light. Each of the fluorescent light early photon portions is a portion of the fluorescent light less than all of the fluorescent light associated with a corresponding illumination light pulse, and each of the intrinsic light early photon portions is a portion of the intrinsic light less than all of the intrinsic light associated with the corresponding illumination light pulse. The system also includes an image processor configured to process data corresponding to at least one of the detected fluorescent light early photon portions and/or the detected intrinsic light early photon portions, and the processor is configured to generate a fluorescent light image from the processed data, where the fluorescent light image is representative of a spatial distribution (e.g., 2-D or 3-D distribution) of the fluorescent material in at least two dimensions.

In preferred embodiments, the early photon portion (of fluorescent light and intrinsic light) is a portion that reaches the detector before the remaining light associated with a given light pulse. For example, in certain embodiments, the early photon portion is up to the first 10%, up to the first 20%, up to the first 30%, up to the first 40%, up to the first 50%, up to the first 60%, or up to the first 70% of the light photons associated with a given light pulse that reach the detector. In certain embodiments, the fluorescent light early photon portion for a given illumination light pulse has an associated time extent less than a time extent corresponding to (e.g., delivery of) all fluorescent light photons associated with the given illumination light pulse. Similarly, in certain embodiments, the intrinsic light early photon portion corresponding to a given illumination light pulse has an associated time extent less than a time extent corresponding to all intrinsic light photons associated with the given illumination light pulse. For example, the fluorescent light early photon portion time extent and/or the intrinsic light early photon portion time extent may be less than or equal to about 20%, less than or equal to about 30%, less than or equal to about 40%, less than or equal to about 50%, less than or equal to about 60%, or less than or equal to about 70% of the time extent corresponding to all fluorescent or intrinsic light photons associated with the given illumination light pulse. In certain embodiments, the fluorescent light early photon time extent is less than or equal to about 500 picoseconds, less than or equal to about 400 picoseconds, less than or equal to about 300 picoseconds, less than or equal to about 200 picoseconds, less than or equal to about 100 picoseconds, less than or equal to about 75 picoseconds, or less than or equal to about 50 picoseconds. In certain embodiments, the intrinsic light early photon time extent is less than or equal to about 500 picoseconds, less than or equal to about 400 picoseconds, less than or equal to about 300 picoseconds, less than or equal to about 200 picoseconds, less than or equal to about 100 picoseconds, less than or equal to about 75 picoseconds, or less than or equal to about 50 picoseconds. In certain embodiments, the spatial extent of the one or more illumination light pulses is less than a dimension of the specimen.

The fluorescent light image may be generated in accordance with a plurality of fluorescent light early photon portions and a plurality of intrinsic light early photon portions corresponding to a plurality of illumination light pulses. For example, the plurality of illumination light pulses may be directed into the specimen at different angles and/or at different positions, resulting in a plurality of projections. Fluorescent and intrinsic light early photon portions may be detected that correspond to each of these projections, and a tomographic image may be projected by the image processor using the detected photon portions.

In some embodiments, the early-photon light detector is configured to generate a fluorescent light measurement corresponding to the one or more fluorescent light early photon portions, and is configured to generate an intrinsic light measurement corresponding to the one or more intrinsic light early photon portions, wherein the image processor is configured to generate the fluorescent light image using the fluorescent light measurement and the intrinsic light measurement. In some embodiments, the light source and/or the early-photon light detector is spatially separated from the specimen so that the illumination light and/or the detected fluorescent light early photon portion(s) travel through air.

The image processor is preferably configured to provide a normalized fluorescent light measurement representative of at least one of the detected fluorescent light early photon portions using the fluorescent light measurement and the intrinsic light measurement. In this way, it is possible to adjust for inhomogeneity of light propagation with the specimen, for example, where the specimen is an inhomogeneous medium, as is a mammal. In certain embodiments, the image processor is configured to provide a tomographic fluorescent light image representative of the spatial distribution of the fluorescent material in three physical dimensions using a model of early-photon propagation in a diffuse medium and using the normalized fluorescent light measurement, thereby adjusting for inhomogeneity of light propagation within the specimen. In preferred embodiments, the specimen is diffuse to propagation of the intrinsic light and the fluorescent light. The specimen may be, for example, a mammal, such as a mouse.

In certain embodiments, the image processor is configured to generate a normalized fluorescent light image representative of the spatial distribution of the fluorescent material in at least two physical dimensions by generating a raw fluorescent light image using the fluorescent light measurement, generating a raw intrinsic light image using the intrinsic light measurement, and combining the raw intrinsic light image and the raw fluorescent light image. In certain embodiments, the image processor is configured to provide a tomographic fluorescent light image representative of the spatial distribution of the fluorescent material in three physical dimensions using a model of early-photon propagation in a diffuse medium and using the normalized fluorescent light measurement, thereby adjusting for inhomogeneity of light propagation within the specimen.

The light source may be configured to direct the illumination light into the specimen at multiple locations, resulting in a plurality of projections. The light source may be configured to transilluminate at least a portion of the specimen, to epi-illuminate the specimen (e.g., to epi-illuminate a portion of the surface of the specimen), or both. The early-photon light detector can be configured to detect the one or more fluorescent light early photon portions and the one or more intrinsic light early photon portions at each of the plurality of projections.

In certain embodiments, the early-photon light detector is configured to move about the specimen to a plurality of positions and to receive the one or more fluorescent light early photon portions and the one or more intrinsic light early photon portions at a plurality of positions. In other embodiments, the detector does not move about the specimen (e.g., where a CCD is used). In certain embodiments, the system further includes a movable stage configured to hold the specimen and move the specimen to a plurality of positions and to receive the one or more fluorescent light early photon portions and the one or more intrinsic light early photon portions at a plurality of positions, resulting in a plurality of projections. In other embodiments, there is no movable stage necessary—e.g., light is introduced into the specimen at various locations (at various projections) as in a raster scan.

There may be one or more light filters disposed between the specimen and the early-photon light detector, where the filter(s) are configured to transmit the one or more fluorescent light early photon portions and to block the one or more intrinsic light early photon portions at a first time, and the filter(s) are also configured to block the one or more fluorescent light early photon portions and to transmit the one or more intrinsic light early photon portions at a second time. In certain embodiments, the system includes a first light filter disposed between the specimen and the early-photon light detector, where the first light filter is configured to transmit the one or more fluorescent light early photon portions and to block the one or more intrinsic light early photon portions; and the system includes a second light filter disposed between the specimen and the early-photon light detector, where the second light filter is configured to block the one or more fluorescent light early photon portions and to transmit the one or more intrinsic light early photon portions.

In certain embodiments, the illumination light has wavelength within a range from about 400 nm to about 1000 nm. For example, the illumination light may have wavelength within a range from about 400 nm to about 700 nm, and/or from about 700 nm to about 1000 nm. In certain embodiments, the illumination light has wavelength from about 400 nm to about 500 nm, from about 500 nm to about 600 nm, from about 600 nm to about 700 nm, from about 700 nm to about 800 nm, from about 800 nm to about 900 nm, or from about 900 nm to about 1000 nm. In certain embodiments, the illumination light comprises or consists of visible light, infrared light, and/or near-infrared light. In certain embodiments, the fluorescent light has wavelength within a range from about 400 nm to about 1000 nm. For example, the fluorescent light may have wavelength within a range from about 400 nm to about 700 nm, and/or from about 700 nm to about 1000 nm. In certain embodiments, the fluorescent light has wavelength from about 400 nm to about 500 nm, from about 500 nm to about 600 nm, from about 600 nm to about 700 nm, from about 700 nm to about 800 nm, from about 800 nm to about 900 nm, or from about 900 nm to about 1000 nm. In certain embodiments, the fluorescent light comprises or consists of visible light, infrared light, and/or near-infrared light.

The fluorescent material may include a fluorescent protein and/or a fluorescent probe, for example. The fluorescent material may include a substance endogenous to the specimen and/or the fluorescent material may include a substance that has been administered to the specimen prior to imaging with the optical imaging system.

In certain embodiments, the system further includes a gate generator coupled to the early-photon light detector and configured to generate a receive gate signal in accordance with the one or more fluorescent light early photon portions and in accordance with the one or more intrinsic light early photon portions detected by the early-photon light detector. The gate generator may further be coupled to the light source and further configured to generate a transmit gate signal to control a duration of the one or more illumination light pulses. The gate generator may further comprise a time delay module configured to generate a time delay signal to provide a time delay between the transmit gate signal and the receive gate signal. For example, the time delay module may provide different time delays for the one or more fluorescent light early photon portions detected by the early-photon light detector than for the one or more intrinsic light early photon portions detected by the early-photon light detector.

In certain embodiments, the early-photon light detector includes a gatable image intensifier. The early-photon detector may also (or alternatively) include a time-to-amplitude converter.

The description of elements of the embodiments of one or more other aspects of the invention can be applied to this aspect of the invention as well.

In another aspect, the invention is directed to a method of providing a representation of a spatial distribution of fluorescent material within a specimen, the method including: (a) directing a pulse of excitation light into a specimen at one or more locations, the excitation light becoming intrinsic light within the specimen and the intrinsic light exiting the specimen; (b) detecting an intrinsic light early photon portion exiting the specimen, wherein the intrinsic light early photon portion is a portion of the intrinsic light less than all of the intrinsic light corresponding to the pulse of excitation light; (c) detecting a fluorescent light early photon portion exiting the specimen, wherein the fluorescent light early photon portion is a portion of fluorescent light produced from fluorescent material within the specimen as a result of the pulse of excitation light, and wherein the fluorescent light early photon portion is less than all of the fluorescent light produced from the fluorescent material within the specimen as a result of the pulse of excitation light; and (d) processing data corresponding to both the detected intrinsic light and the detected fluorescent light to generate a representation of a spatial distribution of the fluorescent material within the specimen.

In certain embodiments, it is possible to combine data corresponding to the early-arriving photons corresponding to the pulsed excitation light with data corresponding to continuous wave (CW) excitation light and/or frequency-modulated (FM) excitation light. For example, early-arriving photon data may be used to obtain information about fluorescence lifetime and CW and/or FM data may be used for robust quantification.

For example, in certain embodiments, the method further includes directing continuous wave (CW) excitation light into the specimen; and detecting CW fluorescent light exiting the specimen, where the CW fluorescent light is produced from the fluorescent material within the specimen as a result of the CW excitation light, and wherein step (d) further includes using data corresponding to the detected CW fluorescent light in generating the representation of the spatial distribution of the fluorescent material within the specimen. In certain embodiments, the method further includes detecting CW intrinsic light exiting the specimen corresponding to the CW excitation light, wherein step (d) further includes using data corresponding to the detected CW intrinsic light in generating the representation of the spatial distribution of the fluorescent material within the specimen.

In another example, in certain embodiments, the method further includes directing frequency-modulated (FM) [also referred to as intensity-modulated (IM)] excitation light into the specimen; and detecting FM fluorescent light exiting the specimen produced as a result of the FM excitation light, wherein step (d) further includes using data corresponding to the detected FM fluorescent light in generating the representation of the spatial distribution of the fluorescent material within the specimen. In certain embodiments, the method further includes detecting FM intrinsic light exiting the specimen corresponding to the FM excitation light, wherein step (d) further includes using data corresponding to the detected FM intrinsic light in generating the representation of the spatial distribution of the fluorescent material within the specimen.

The method may include generating a fluorescent light measurement corresponding to the fluorescent light early photon portion and generating an intrinsic light measurement corresponding to the intrinsic light early photon portion, wherein step (d) includes using the fluorescent light measurement and the intrinsic light measurement in generating the representation.

In certain embodiments, step (d) includes generating a tomographic representation of a three-dimensional distribution of the fluorescent material within the specimen.

In certain embodiments, the illumination light (and/or excitation light) has wavelength within a range from about 400 nm to about 1000 nm. For example, the illumination light may have wavelength within a range from about 400 nm to about 700 nm, and/or from about 700 nm to about 1000 nm. In certain embodiments, the illumination light has wavelength from about 400 nm to about 500 nm, from about 500 nm to about 600 nm, from about 600 nm to about 700 nm, from about 700 nm to about 800 nm, from about 800 nm to about 900 nm, or from about 900 nm to about 1000 nm. In certain embodiments, the illumination light comprises or consists of visible light, infrared light, and/or near-infrared light. In certain embodiments, the fluorescent light has wavelength within a range from about 400 nm to about 1000 nm. For example, the fluorescent light may have wavelength within a range from about 400 nm to about 700 nm, and/or from about 700 nm to about 1000 nm. In certain embodiments, the fluorescent light has wavelength from about 400 nm to about 500 nm, from about 500 nm to about 600 nm, from about 600 nm to about 700 nm, from about 700 nm to about 800 nm, from about 800 nm to about 900 nm, or from about 900 nm to about 1000 nm. In certain embodiments, the fluorescent light comprises or consists of visible light, infrared light, and/or near-infrared light.

The fluorescent material may include a fluorescent protein and/or a fluorescent probe, for example. The fluorescent material may include a substance endogenous to the specimen and/or the fluorescent material may include a substance that has been administered to the specimen prior to imaging with the optical imaging system.

In preferred embodiments, the early photon portion (of fluorescent light and intrinsic light) is a portion that reaches the detector before the remaining light associated with a given light pulse. For example, in certain embodiments, the early photon portion is up to the first 10%, up to the first 20%, up to the first 30%, up to the first 40%, up to the first 50%, up to the first 60%, or up to the first 70% of the light photons associated with a given light pulse that reach the detector. In certain embodiments, the fluorescent light early photon portion for a given illumination light pulse has an associated time extent less than a time extent corresponding to (e.g., delivery of) all fluorescent light photons associated with the given illumination light pulse. Similarly, in certain embodiments, the intrinsic light early photon portion corresponding to a given illumination light pulse has an associated time extent less than a time extent corresponding to all intrinsic light photons associated with the given illumination light pulse. For example, the fluorescent light early photon portion time extent and/or the intrinsic light early photon portion time extent may be less than or equal to about 20%, less than or equal to about 30%, less than or equal to about 40%, less than or equal to about 50%, less than or equal to about 60%, or less than or equal to about 70% of the time extent corresponding to all fluorescent or intrinsic light photons associated with the given illumination light pulse. In certain embodiments, the fluorescent light early photon time extent is less than or equal to about 500 picoseconds, less than or equal to about 400 picoseconds, less than or equal to about 300 picoseconds, less than or equal to about 200 picoseconds, less than or equal to about 100 picoseconds, less than or equal to about 75 picoseconds, or less than or equal to about 50 picoseconds. In certain embodiments, the intrinsic light early photon time extent is less than or equal to about 500 picoseconds, less than or equal to about 400 picoseconds, less than or equal to about 300 picoseconds, less than or equal to about 200 picoseconds, less than or equal to about 100 picoseconds, less than or equal to about 75 picoseconds, or less than or equal to about 50 picoseconds. In certain embodiments, the spatial extent of the one or more illumination light pulses is less than a dimension of the specimen.

In preferred embodiments, the specimen is diffuse to propagation of the intrinsic light and the fluorescent light. The specimen may be, for example, a mammal, such as a mouse.

The method may include directing illumination light into the specimen at multiple locations, resulting in a plurality of projections that transilluminate at least a portion of the specimen, or that epi-illuminate the specimen (e.g., that epi-illuminate a portion of the surface of the specimen), or both transilluminate and epi-illuminate the specimen. The method may include detecting the one or more fluorescent light early photon portions and the one or more intrinsic light early photon portions at each of the plurality of projections and use data corresponding to these data to generate a tomographic representation of the spatial distribution of the fluorescent material within the specimen (e.g., a 3-D tomographic map).

The description of elements of the embodiments of one or more other aspects of the invention can be applied to this aspect of the invention as well.

In accordance with another aspect of the present invention, a system for optical imaging includes a light source adapted to project illumination light, comprising one or more illumination light pulses, toward a specimen having a fluorescent material therein (including both exogenously administered or genetically engineered fluorescent material or biologically natural endogenous fluorescent material). The illumination light includes excitation light. The illumination light enters the specimen becoming intrinsic light within the specimen. The excitation light is adapted to excite fluorescent light from the fluorescent material. The fluorescent light and the intrinsic light exit the specimen. The system further includes an early-photon light detector adapted to receive one or more fluorescent light early photon portions associated with the fluorescent light and one or more intrinsic light early photon portions associated with the intrinsic light. Each fluorescent light early photon portion is a portion of the fluorescent light less than all of the fluorescent light associated with a respective illumination light pulse. Each fluorescent light early photon portion has a fluorescent light early photon portion time extent. Each intrinsic light early photon portion is a portion of the intrinsic light less than all of the intrinsic light associated with a respective illumination light pulse. Each intrinsic light early photon portion has an intrinsic light early photon time extent. The early-photon light detector is constructed to generate a fluorescent light measurement using only the one or more fluorescent light early photon portions. The early-photon light detector is also gated to generate an intrinsic light measurement using only the one or more intrinsic light early photon portions. The system further includes an image processor coupled to receive and process the fluorescent light measurement and the intrinsic light measurement to generate a processed fluorescent light image representative of a spatial distribution of the fluorescent material in at least two physical dimensions.

The description of elements of the embodiments of one or more other aspects of the invention can be applied to this aspect of the invention as well.

In accordance with another aspect of the present invention, a method of optical imaging includes projecting light with a light source adapted to project illumination light, comprising one or more illumination light pulses, toward a specimen having a fluorescent material therein. The illumination light includes excitation light. The illumination light enters the specimen becoming intrinsic light within the specimen. The excitation light is adapted to excite fluorescent light from the fluorescent material. The fluorescent light and the intrinsic light exit the specimen. The method further includes receiving with an early-photon light detector one or more fluorescent light early photon portions associated with the fluorescent light and one or more intrinsic light early photon portions associated with the intrinsic light. Each fluorescent light early photon portion is a portion of the fluorescent light less than all of the fluorescent light associated with a respective illumination light pulse. Each fluorescent light early photon portion has a fluorescent light early photon portion time extent. Each intrinsic light early photon portion is a portion of the intrinsic light less than all of the intrinsic light associated with a respective illumination light pulse. Each intrinsic light early photon portion has an intrinsic light early photon time extent. The method further includes an early-photon light detector to generate a fluorescent light measurement using only the one or more fluorescent light early photon portions. The method further includes an early-photon light detector to generate an intrinsic light measurement using only the one or more intrinsic light early photon portions. The method also includes processing with an image processor the fluorescent light measurement and the intrinsic light measurement to generate a processed fluorescent light image representative of a spatial distribution of the fluorescent material in at least two physical dimensions.

The description of elements of the embodiments of one or more other aspects of the invention can be applied to this aspect of the invention as well.

BRIEF DESCRIPTION OF THE DRAWINGS

The foregoing features of the invention, as well as the invention itself may be more fully understood from the following detailed description of the drawings, in which.

DETAILED DESCRIPTION OF THE INVENTION

Figure 1:
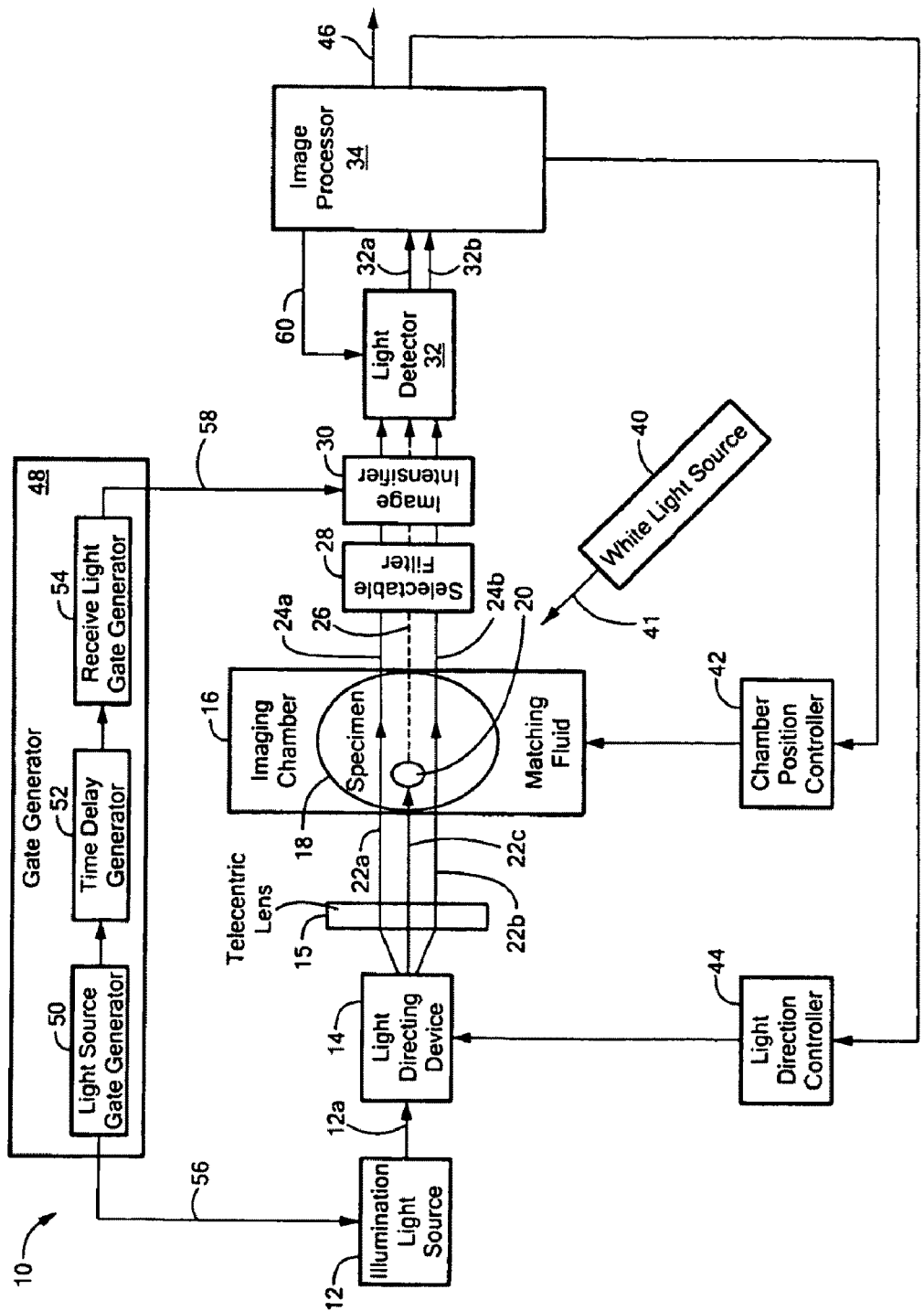
FIG. 1 is a block diagram showing a system for optical tomography, having a transillumination light source, a light detector, and an image processor.

It is contemplated that methods, systems, and processes described herein encompass variations and adaptations developed using information from the embodiments described herein.

Throughout the description, where systems are described as having, including, or comprising specific components, or where processes and methods are described as having, including, or comprising specific steps, it is contemplated that, additionally, there are systems of the present invention that consist essentially of or consist of, the recited components, and that there are processes and methods of the present invention that consist essentially of, or consist of, the recited processing steps.

Before describing the systems and methods for optical imaging, some introductory concepts and terminology are explained. As used herein, the term "phantom" is used to describe a test object being imaged. A phantom is typically an article having diffuse light propagation characteristics similar to living tissue, for example, a piece of appropriately engineered resin block. For another example, a phantom can be a vial, which contains cells having fluorescent proteins therein, a fluorescent marker, or a fluorochrome.

As used herein, the term "diffuse" is used to describe light having photons that have encountered several scattering events (for example, more than ten scattering events) when propagating inside a medium, independent of absorption of the photons in the medium. The term diffuse is also used herein to describe the medium which is responsible for the scattering events.

As used herein, the term "fluorescent material" is used to describe a fluorochrome, a fluorescent probe, or a fluorescent protein. In general, the fluorescent material tends to concentrate at a tumor or lesion. Fluorescent material may be administered to a specimen (exogenous) or endogenous to the specimen (e.g., fluorescent material within the specimen). Various probes that may be used in systems and methods described herein include, for example, (1) probes that become activated after target contact (e.g., binding or interaction) (Weissleder et al., Nature Biotech., 17:375-378, 1999; Bremer et al., Nature Med., 7:743-748, 2001), (2) wavelength shifting beacons (Tyagi et al., Nat. Biotechnol., 18:1191-1196, 2000), (3) multicolor fluorescence probes (Tyagi et al., Nat. Biotechnol., 16:49-53, 1998), or (4) probes that have high binding affinity to targets, i.e., that remain within a target region while non-specific probes are cleared from the body (Achilefu et al., Invest. Radiol., 35:479-485, 2001; Becker et al., Nature Biotech. 19:327-331, 2001; Bujai et al., J. Biomed. Opt. 6:122-133, 2001; Ballou et al. Biotechnol. Prog. 13:649-658, 1997; and Neri et al., Nature Biotech. 15:1271-1275, 1997), and/or (5) traditional contrast agents such as gadolinium or iodine based imaging agents. The texts of the above-referenced documents are incorporated herein by reference in their entirety. For example, molecular imaging probes may be used in methods and systems described herein. A molecular imaging probe is a probe that is targeted to a molecular structure, such as a cell-surface receptor or antigen, an enzyme within a cell, or a specific nucleic acid, e.g., DNA, to which the probe hybridizes.

The term "fluorochrome" as used herein will be understood to describe a type of known biocompatible dye or other fluorescence agent that can be systemically or topically (e.g., locally) applied to a biological tissue. Some fluorochromes are target fluorochromes, which tend to congregate at certain anatomical, functional, or molecular features in the tissue, including for example, at cancerous or inflammatory lesions. Other fluorochromes include, for example, fluorescent particles such as Quantum dots, Silicon fluorescent nanoparticles, and the like.

As used herein, the term "excitation light" is used to describe at least a part of light generated by an "illumination light source" that is incident upon a biological tissue. The excitation light has a wavelength that can excite fluorescent light from a fluorescent material within the tissue. The excitation light can be monochromatic, or it can cover a broader spectrum, for example, white light. The fluorescent light can be received by a light detector (e.g., a camera) resulting in a so-called "fluorescent light image" of the tissue and/or fluorescent material at a selected different wavelength than the wavelength of the excitation light. The excitation light can also itself interact with the tissue, and can be received by the light detector at the same wavelength (excitation wavelength) as that at which it was transmitted by the excitation light source.

As used herein, the term "incident light" or "illumination light" is used to generally describe light that is generated by the illumination light source. The illumination light can include not only the excitation light having a wavelength selected to excite fluorescent light from the fluorescent material, but also light having other wavelengths. However, in some arrangements, the illumination light can include only the excitation light having a particular wavelength or band of wavelengths that excite fluorescent light from the fluorescent material. The illumination light does not necessarily include the excitation light at all times. The wavelengths of the illumination light can be generated simultaneously or at different times.

As used herein, the term "intrinsic light" is used to refer to illumination light that has entered a biological tissue and may or may not include excitation light able to excite fluorescent light from fluorescent material within biological tissue. Upon exiting the biological tissue, the intrinsic light can be used to generate a so-called "intrinsic light image" of the tissue. The intrinsic light image is either an image obtained at the same wavelength as the wavelength of the excitation light (i.e., an intrinsic excitation light image), an image obtained at a different wavelength than the wavelength of the excitation light, or an image obtained by a combination of images obtained at a variety of wavelengths, which may or may not include the wavelength of the excitation light. In general, the intrinsic light image can be generated from one or more wavelengths of light in the illumination light that are at different wavelengths than the wavelength(s) of the emitted fluorescent light used to generate a fluorescent light image associated with the fluorescent light.

As used herein, the term "apparent light sources" is used to describe projections of a single illumination light source to a plurality of physical positions or angles, each providing an apparent light source directed at a different respective direction toward the biological tissue.

In general, it will be understood that an intrinsic light image is an image of natural structures inside the tissue, generally exclusive of fluorescence of the tissue or of fluorescent light generated by fluorescent material within the tissue, although experimentally some contamination may occur. In contrast, a fluorescent light image is an image generated as a result of the tissue fluorescence or of fluorescent light generated by the fluorescent material within the tissue, which may be affected by natural structures in the tissue.

As used herein, the term "epi-illumination light source" is used to describe an illumination light source that can generate illumination light (also referred to herein as "epi-illumination light"), including excitation light, that reflects from a surface of biological tissue and/or that propagates into the biological tissue, wherein the excitation light is able to excite a fluorescent material in or on the tissue. To form an epi-illumination image, image light is collected generally on the same side of the tissue as the epi-illumination light source. An epi-illumination image can be either an intrinsic light epi-illumination image or a fluorescent light epi-illumination image.

As used herein, the term "transillumination light source" is used to describe a light source that can generate illumination light (also referred to herein as "transillumination light") including excitation light, that propagates into the tissue, wherein the excitation light is able to excite a fluorescent material in or on the tissue. To form a transillumination image, light is collected generally on the opposite side of the tissue from the transillumination light source. Like an epi-illumination image, a transillumination image can be either an intrinsic light transillumination image or a fluorescent light transillumination image.

In some arrangements, the epi-illumination light source and/or the transillumination light source(s) can, more generally generate illumination light, which includes not only light having a wavelength of the excitation light, but also other wavelengths.

To generate an intrinsic light epi-illumination image, the illumination light is received by a light detector (e.g., camera) after being directed back from (e.g., reflected from) an object being imaged. In contrast, to generate an intrinsic light transillumination image, the illumination light is received by a light detector (e.g., camera) after it passes through the object being imaged.

Similarly, to generate a fluorescent light epi-illumination image, the excitation light (epi-illumination light) excites fluorescence on or in the tissue, which is directed back from tissue being imaged, and which is received by a light detector (e.g., camera) at a wavelength different from the illumination light. To generate a fluorescent light transillumination image, the excitation light also excites fluorescence in the tissue, which is directed through the tissue being imaged, and which is received by a light detector (e.g., camera) at a wavelength different from the excitation light.

As used herein, the term "image" is used to describe a visual representation of the physical distribution (e.g., concentration) of chromophores, scatterers, fluorochromes, and/or other objects. The image can also be representative of a visual representation of the physical distribution of light. An image may be generated from "optical measurements" (fluorescent light measurement and/or intrinsic light measurements) collected by a camera or other light detector. As will become apparent from discussion below, the optical measurements can be processed to generate "processed optical measurements," which can result in a so-called "processed fluorescent light image." The processed fluorescent light image can be displayed as an image on a computer monitor. The visual representation provided by the processed fluorescent light image is representative of a spatial distribution (e.g., concentration distribution) of the fluorescent material in at least two physical dimensions (i.e., a planar image or a two dimensional tomographic image) or it can be indicative of three physical dimensions (i.e., a tomographic image). The processed fluorescent light image can represent concentrations of the fluorescent material by colors, grey scale, textures, or any other means.

The above optical measurements can be point optical measurements, linear optical measurements, or planar optical measurements.

Among the systems and methods described herein are fluorescence molecular tomography (FMT) systems, which produce tomographic images of the distribution of a fluorescent material in a specimen. An illustrative FMT system is described in U.S. Patent Application Publication No. US2004/0015062, the text of which is incorporated by reference herein, in its entirety. The text of the following documents is incorporated herein by reference and this subject matter may be applied in the embodiments described herein: U.S. Pat. No. 6,615,063; U.S. Patent Application Publication No. US2004/0015062; International (PCT) Patent Application Publication No. WO03/102558; International (PCT) Patent Application Publication No. WO2004/072906; and International (PCT) Patent Application Publication No. WO2007/111669.

The FMT systems described herein do not require either direct contact or optical contact between the light sources/detectors and the object to be imaged, although systems that use direct contact or direct optical contact (e.g., the latter by use of index-matching fluids) are included herein. FMT systems that do not require direct contact or optical contact with the object to be imaged account for heterogeneities of the index of refraction within and surrounding the animal tissue, which give rise to photon reflections at the boundaries. See, for example, International (PCT) Application Publication No. WO 03/102558, published 11 Dec. 2003; and R. Schulz, J. Ripoll and V. Ntziachristos, "Experimental Fluorescence Tomography of Tissues with Noncontact Measurements," IEEE Transactions on Medical Imaging, Vol. 23, No. 4, pp. 492-500 (2004), the texts of which are incorporated herein by reference, in their entirety. These techniques are further augmented by the use of so-called free-space transformations, which take into account the presence of a non-turbid medium (air) between the object to be imaged and the detectors. See, for example, International (PCT) Application Publication No. WO 2004/072906, published 26 Aug. 2004; and J. Ripoll, R. Schulz and V. Ntziachristos, "Free-Space Propagation of Diffuse Light: Theory and Experiments," Physical Review Letters, Vol. 91 No. 10 (2003), the texts of which are incorporated herein by reference, in their entirety.

The systems and methods described herein refer to the use of particular types of light or light having particular characteristics. For example, reference is made to systems and methods using near-infrared excitation light, which provides particular benefits in the near-infrared (NIR) wavelength range of about 650-1000 nm. It should, however, also be appreciated that the systems and methods described herein can also be applied to excitation light having other wavelengths, for example, to light in the visible range of about 400 nm-650 nm. Also, the systems and methods apply to a system in which excitation light is at one wavelength range, for example, in the visible range, and the fluorescent light emitted by fluorescent material is in another wavelength range, for example in the NIR range. The systems and methods also apply where both the excitation light and the light emitted by the fluorescent material are in the NIR range. In addition, excitation light and/or emitted light having a wavelength at the interface of the visible range and near-infrared range can be used, for example in the 550 nm-650 nm range. The excitation light can have the same intensity at all wavelengths therein, or it can have predetermined attenuation of selected wavelengths, e.g., by using appropriate filters. Also, excitation light beyond the wavelength range of 400 nm to 1000 nm can be used.

As used herein, the term "early photons" refers to an early part of the light received at a light detector in response to a short pulse of illumination light. The early photons have an early photon time extent generally in accordance with a time difference between a shortest light propagation path and a longest light propagation path from an illumination light source to a light detector. The differences in light paths can be generally attributed to photon scattering, particularly when the tissue through which the photons propagate is highly scattering and appears diffuse to the propagation of light. Early photons can be characterized as being representative of a particular portion or percentage of a total number of photons received by a light detector in response to the illumination light pulse, characterized by arrival times that are generally shorter than other photon portions.

The early photon time extent is somewhat different depending upon the medium (i.e., specimen) and the size to the medium through which the light propagates. Fluorescent light early photons are associated with the fluorescent light while intrinsic light early photons are associated with the intrinsic light.

It will become apparent from discussion below in conjunction with FIG. 3 that, in accordance with the systems and methods described herein, only the early photons are used to generate fluorescent light images and/or intrinsic light images having improved quality when compared to images that would be generated using more of the photons or all of the photons received by an early-photon light detector in response to a pulse of illumination light. It will also become apparent from discussion below in conjunction with FIG. 3, that the early photons used to form images herein can be but a portion (an early potion) of the total number of photons received by the early-photon light detector in response to a pulse of illumination light. Therefore, the terms "early photons" and "early photon portion" are used synonymously herein. The term "early photon portion" is particularly indicative of an early portion of the total photons received in response to one pulse of illumination light. The early photon portion has a time extent generally in accordance with a time difference between a shortest light propagation path and another light propagation path less than the longest light propagation path described above.

As described above, the early photons (or early photon portion) can be characterized as a portion or percentage of the total number of photons received by the early-photon light detector in response to a pulse of illumination light. For example, the early photons can be within the first ten percent of the total received photons, within the first twenty percent, within the first thirty percent, within the first forty percent, or within the first fifty percent. The early photon portion need not begin at the first received photon, but can be offset in time to begin at a time delay after the first received photon.

In general, it will be understood that on average, the early photons have straighter propagation paths (i.e., fewer scattering events) than photons arriving later at a light detector in response to a pulse of illumination light.

Referring to FIG. 1, a system 10 for optical imaging includes an illumination light source 12, which can generate illumination light 12a, and a light directing device 14 to provide a plurality of apparent light sources (i.e., light paths). The apparent light sources provide apparent illumination light 22a-22c at a variety of positions or directions relative to a specimen 18. While three such positions or directions are shown, there can be more than three or fewer than three apparent light source positions. Apparent illumination light from the apparent light sources, depicted as arrows 22a-22c, passes through a lens 15, for example, a telecentric lens, resulting in substantially parallel light paths 22a-22c.

The light directing device 14 can include, for example, one or more movable mirrors, controlled by a light direction controller 44. With this arrangement, only one illumination light source 12 need be provided in order to achieve a plurality of apparent light sources. Alternatively, in some arrangements described more fully below, the illumination light may include no scanning methodology, (e.g., no light directing device 14) but instead can be a broad (planar) illumination field. Other possible arrangements include the use of a raster scan approach with one or more CCD detector arrays, and the like. For example, light is introduced into the specimen at various locations (at various projections) in a raster scan pattern from a single (or multiple), preferably movable, optical fiber(s).

Apparent illumination light 22a-22c, which can include, but is not limited to, excitation light, impinges upon the specimen 18, becoming intrinsic light upon entry, and exits the specimen 18 as intrinsic light 24a, 24b. The intrinsic light 24a, 24b can pass through a selectable light filter 28, through a gatable image intensifier 30, and is received by a light detector 32, serving as the early-photon detector. The early photon detector utilizes appropriate technology that can separate the arrival time of individual photons or bulk of photons. This can be achieved for example via time-resolved or time-gated techniques using, for example, a time-to-amplitude converter. The apparent illumination light 22b also propagates into the specimen 18 and impinges upon fluorescent material 20 within the specimen 18. In response to the excitation light (having a wavelength selected to excite fluorescent light) of the apparent illumination light 22c, fluorescent material 20 within the specimen 18 emits fluorescent light 26, which also passes through the selectable light filter 28, through the gated image intensifier 30, and is received by the light detector 32. The gatable image intensifier 30 in combination with the light detector 32 are referred to herein as a "early-photon light detector." It is to be understood that while illumination light at the excitation wavelength is required to produce early photon fluorescence light, the intrinsic light collected for normalization purposes may include or may not include light at the excitation wavelength.

An optional white light source 40 can provide further illumination of the specimen as white light 41, to provide other light paths (not shown), which reflect from a surface of the specimen, and which can also pass through the selectable light filter 28, through the gated image intensifier 30, and can be received by the light detector 32. The white light source can essentially provide a white light image of the specimen 18 that can be overlaid on other images described below.

In some embodiments, the intrinsic light 24a, 24b and the fluorescent light 26 nearly simultaneously exit the specimen 18. In this arrangement, the intrinsic light 24a, 24b and the fluorescent light 26 can be separated by the selectable filter 28, to provide the different lights to the light detector 32 at the same time or at separate times. To this end, the selectable filter can be centered at different times on the wavelength of the intrinsic light 24a, 24b or of the fluorescent light 26. However, in some other arrangements, a system can include a plurality of light paths, each having a dedicated light filter 28, gatable image intensifier 30, and light detector 32. For example, in one particular embodiment one light filter, gatable image intensifier, and light detector can generate optical measurements of the fluorescent light 26, and another light filter 28, gatable image intensifier 30, and light detector 32 can generate optical measurements of the intrinsic light 24a, 24b. This particular arrangement can utilize a dedicated filter in each optical path and a light directing device, such as a dichroic mirror that can directs fluorescent and excitation light to different light detectors.

The early photons associated with the intrinsic light 24a, 24b tend to arrive, on average, at the light detector 32 before the early photons associated with the fluorescent light 26, in part because the fluorescent material 20 has a finite time before it is excited by the apparent illumination light 22c.

In some arrangements, by way of the gated image intensifier, the system 10 can form images using only early photons. The early photons (early photon portion) can include early fluorescent light photons associated with the fluorescent light 26 and/or early intrinsic light photons associated with the intrinsic light 24a, 24b. In some other arrangements, the system 10 can use, for example, only early photons within the first approximately ten percent, twenty percent, thirty percent, forty percent, or fifty percent of all received photons associated with an illumination light pulse. However, the early photons that are used can be other percentages of all of the received photons associated with an illumination light pulse.

In some embodiments, two or more fluorescent materials (e.g., chromophores) can be used within the specimen 18. In these embodiments, the illumination light source 12 can generate illumination light having a respective two or more excitation lights, each with a respective wavelength that can excite one of the different fluorescent materials. These embodiments can have two or more optical paths, each path to receive the intrinsic light and fluorescent light for each fluorescent material.

The light detector 32 operates to convert the received light into digital data 32a, 32b (also referred to herein as "optical measurements"). The optical measurements can include a "fluorescent light measurement" 32a and an "intrinsic light measurement" 32b, at substantially the same time or at different times.

An image processor 34 receives the optical measurements 32a, 32b and generates processed fluorescent light image data resulting in a "processed fluorescent light image" 46. In some embodiments, the processed fluorescent light image 46 is a tomographic image having three spatial dimensions (which can be viewed as individual two-dimensional slices). In some other embodiments, the processed fluorescent light image 46 is a planar image having two spatial dimensions.

In some arrangements, the image processor 34 is operable to combine the fluorescent light measurements 32a associated with the fluorescent light 26 with the intrinsic light measurements 32b associated with the intrinsic light 24a, 24b resulting in the above-described processed fluorescent light image 46. The processed fluorescent light image 46 has a greater accuracy than an image that could be generated from the fluorescent light measurements 32a alone, since the image processor 34 can account for the effects of tissue optical heterogeneity in the resulting processed fluorescent light image 46. Generation of the processed fluorescent light image 46 is described below in greater detail in conjunction with FIGS. 1B and 1C. In some arrangements, the white light 41 can be used to generate a white light image that can be superimposed with the processed fluorescent light image 46.

Details of exemplary image processors 34 are described below in conjunction with FIGS. 1B and 1C.

The system 10 can also include the light direction controller 44 to direct the apparent light sources toward predetermined light paths. The system 10 can also include a chamber position controller 42 that can be used to move an imaging chamber 16 to provide more apparent light sources, i.e., the intrinsic light passes through the specimen 18 along additional predetermined light paths.

It should be appreciated that the system 10 provides a transillumination imaging system for which light generated by the illumination light source 12 passes through the specimen 18 and is received generally on the other side of the specimen 18.

It should be understood that the system 10 can be used to generate planar fluorescent light images of the fluorescent material 20, representative of a spatial distribution (e.g., concentration) of the fluorescent material 20 in two physical dimensions, and also to generate tomographic fluorescent light images of the fluorescent material 20, representative of a spatial distribution (e.g., concentration) of the fluorescent material 20 in three physical dimensions.

In some arrangements, the illumination light 12a is generated as a narrow illumination light beam, narrow in two dimensions (e.g., a point illumination on the surface of the specimen 18). In some other arrangements, the illumination light 12a is generated as an illumination light beam wide in one dimension and narrow in another dimension (e.g., a line illumination on the surface of the specimen 18). In some other arrangements, the illumination light 12a is generated as an illumination light beam wide in two dimensions (e.g., a plane illumination on the surface of the specimen 18) that can illuminate a substantial portion of a surface of the specimen.

For some planar imaging arrangements for which the illumination light 12a provides a point illumination, the light directing device 14 can sweep a direction of the apparent light sources (e.g., 22a-22c point illuminations) in one dimension upon the specimen 18 and the specimen 18 can be rotated or moved via the chamber position controller 42 in order to provide another dimension required for two-dimensional planar imaging. For some other planar imaging arrangements for which the illumination light 12a provides a point illumination, the light directing device 14 can sweep a direction of the apparent light sources (e.g., 22a-22c point illuminations) in two dimensions required for two-dimensional planar imaging and the specimen 18 can remain stationary. For arrangements in which the specimen 18 can remain stationary, the chamber position controller 42 is superfluous and can be omitted. For some tomographic imaging arrangements for which the illumination light 12a provides a point illumination, the light directing device 14 can sweep a direction of the apparent light sources (e.g., 22a-22c point illuminations) in two dimensions upon the specimen 18 and the specimen 18 can be rotated or moved via the chamber position controller 42 in order to provide another dimension (i.e., projections) (technically not required, but useful) for three-dimensional tomographic imaging.

For some planar imaging arrangements for which the illumination light 12a provides a line illumination, the light directing device 14 can sweep a direction of the apparent light sources (e.g., 22a-22c line illuminations) in one dimension upon the specimen 18 and the specimen 18 can remain stationary. For arrangements in which the specimen 18 can remain stationary, the chamber position controller 42 is superfluous and can be omitted. For some tomographic imaging arrangements for which the illumination light 12a provides a line illumination, the light directing device 14 can sweep a direction of the apparent light sources (e.g., 22a-22c line illuminations) in one dimension upon the specimen 18 and the specimen 18 can be rotated or moved via the chamber position controller 42 in order to provide another dimension for three-dimensional tomographic imaging. In certain embodiments, light sources and/or photon detectors can be associated with a catheter, an endoscope, for example, in planar imaging. The light sources and/or photon detectors may be separated or part of the same unit, and/or they may be hand-held and/or used intraoperatively.

For some planar imaging arrangements for which the illumination light 12a provides a plane illumination, the light directing device 14 is superfluous and can be omitted resulting in but one apparent light source (e.g., 22a-22c as one plane illumination) illuminating a substantial portion of a surface of the specimen 18 nearest the illumination light source, and the specimen can remain stationary. For some tomographic imaging arrangements for which the illumination light 12a provides a plane illumination, the light directing device 14 is again superfluous and can be omitted resulting in but one apparent light source (e.g., 22a-22c as one plane illumination) illuminating a substantial portion of a surface of the specimen 18 nearest the illumination light source 12, and the specimen can be rotated or moved via the chamber position controller 42 in order to provide another dimension for three-dimensional tomographic imaging.

It should be appreciated that, for embodiments in which the illumination light source 12 provides either point illumination or line illumination of the specimen 18, the optical measurements 32a, 32b are less than what may be considered to be a full image. The optical measurements 32a, 32b however, can be combined into an un-processed image, or they can be separately processed to result in the processed fluorescent light image 46, described more fully below. For embodiments in which the illumination light source generates a plane illumination, the optical measurements 32a, 32b can essentially be a raw fluorescent light image 32a and a raw intrinsic light image 32b, respectively, which can be processed to provide the processed fluorescent light image 46.

For some arrangements, the illumination light 12a can be provided to the light directing device 14 via an optical fiber (not shown). In other arrangements, the illumination light 12a can be provided to the light directing device 14 through the air or through another medium. In some arrangements, the apparent light 22a-22c can propagate though the air or though another medium to the specimen 18. In some arrangements, the intrinsic light 24a, 24b and the fluorescent light 26 can propagate through the air or through another medium to the selectable filter 28.

It should be appreciated that the above arrangements allow the systems and methods described herein to achieve so called "high spatial sampling." In other words, the light directing device 14, which can direct apparent light sources (e.g., 22a-22c) through the air to the specimen 18 and through the air to the selectable light filter 28, in combination with the illumination light pulse and use of received early photons can result in an ability to generate optical measurement of the received light at a great number of physical position in very little time.

In general, spatially-dependent attenuation of the apparent illumination light 22a-22c (or of the received fluorescent and/or intrinsic light 24a, 24b, 26) may be desired in order to reduce the dynamic range of the measurements, i.e. the difference between the lowest and the highest levels of the measured light. When working with single source or single detector measurements, the spatially-dependent attenuation can be achieved by selectively modulating the light power or detector gain as a function of position upon the specimen 18 in order to operate at an optimal signal strength. In some embodiments, spatially-dependent attenuation can be achieved by a feed-back loop or automatic gain control, or by using a pre-determined set of spatially-dependent attenuation values. When operating with broader light fields (e.g., plane illumination), field conditioning using spatially varying attenuation media (not shown) in front of the illumination light source 12 or light detector 32 may be desired.

In some other arrangements, the light directing device 14 delivers the apparent illumination light 22a-22c by way of an optical fiber that can be mechanically translated in two dimensions. The light can then be received by the light detector 32 on the opposite side of the specimen 18. The optical receiving components 28, 30, 32 can be stationary (e.g. a time-gated CCD camera or multitude of time-resolving detectors). However, in other arrangements, the receiving optical components 28, 30, 32 can also be translated in two dimensions so that they are co-axial with the apparent light source paths 22a-22c. In this case the light detector 32 can be a time-resolved photomultiplier tube (PMT). In some other arrangements two or more optical fiber and light detector pairs are translated simultaneously across the specimen 18.

In operation, the apparent illumination light 22a-22c propagates from light directing device 14 (or from the illumination light source 12 when no light directing device 14 is used) toward the specimen 18 via the air (or another medium) and the intrinsic light 24a-24b and fluorescent light 22c also propagate through the air (or another medium) to the selectable filter 28, image intensifier 30, and light detector 32.

In operation, the illumination light source 12 can generate the illumination light 12a in illumination light pulses. In some arrangements, a spatial extent of some or all of the illumination light pulses is less than a dimension of the specimen 18.

To this end, the system 10 can include a gate generator 48, which can include a light source gate generator 50 and a receive light gate generator 54, coupled by a time delay generator 52. The gate generator 48 is operable to generate a receive gate signal 58 in accordance with the early photon portion associated with at least one of the fluorescent light 26 received by the image intensifier 30 or the intrinsic light 24a, 24b received by the image intensifier 30. The gate generator 48 is further operable to generate a transmit gate signal 56 to control a duration and repetition rate of the illumination light pulses. The time delay generator 52 is operable to provide a time delay between an illumination light pulse and a respective receive gate during which the early photon portion (fluorescent light or intrinsic light) is received and collected by the image intensifier 30.

The image intensifier 30 collects only the early photon portion of the fluorescent light 26 and/or of the intrinsic light 24a, 24b, under control of the receive gate signal 58. A control signal 60, which can be synchronous with or asynchronous with the receive gate signal 58, is operable to cause the light detector 32 to generate at least one of the fluorescent light measurement 32a or the intrinsic light measurement 32b. With this arrangement, a plurality of early photon portions associated with a plurality of illumination light pulses can contribute to each fluorescent light measurement 32a and/or to each intrinsic light measurement 32b.

For any one direction of an apparent light source (e.g., 22a, 22b, 22c), the image intensifier 30, by way of the receive gate signal 58, can capture the early photon portions (fluorescent light and intrinsic light) associated with one illumination light pulse or with many illumination light pulses. The image intensifier 30 can provide an intensified image to the light detector 32, which generates the fluorescent light measurement 32a and/or the intrinsic light measurement 32b. It should be understood that collection of the early photon portion associated with many illumination light pulses can improve a signal to noise ratio of resulting light measurements 32a, 32b, and therefore, of the processed fluorescent light image 46.

In some arrangements, each apparent light source pulse 12a is less than about one hundred picoseconds, in some other arrangements, each apparent light source pulse is less than about one picosecond, and in some other arrangements, each apparent light source pulse is less than about 100 femtoseconds. In some arrangements, early photon portions associated with more than one thousand illumination light pulses 12a are collected for each position of an apparent light source and contribute to each light measurement 32a, 32b. In some other arrangements, early photon portions associated with more than ten thousand illumination light pulses are collected and contribute to each light measurement 32a, 32b. In some other arrangements, early photon portions associated with more than ten thousand illumination light pulses are collected and contribute to each light measurement 32a, 32b. In some other arrangements early photons portions associated with more than one hundred thousand illumination light pulses are collected and contribute to each light measurement 32a, 32b. In some other arrangements, early photon portions associated with more than one million illumination light pulses are collected and contribute to each light measurement 32a, 32b. In some other arrangements, early photon portions associated with more than ten million illumination light pulses are collected and contribute to each light measurement 32a, 32b.

In some arrangements, the repetition rate of the illumination light pulses is about eighty million pulses per second. However, the repetition rate can be less than or greater then eighty million pulses per second.

When propagating through the specimen 18, the transmitted illumination light pulses 12a tend to broaden in time. For example, a 100 femtosecond illumination light pulse 12a can broaden to about 1.5 nanoseconds, representative of the light that is received by the image intensifier 30. Nevertheless, in some arrangements, the receive gate 58 can have a pulse width of about 100 picoseconds in order to collect only early photon portions of the received light. A detailed arrangement is described more fully below in conjunction with FIG. 3.

It should be apparent from discussion above that the white light source 40, the chamber position controller 42, the light direction controller 44, and the light directing device 14 are optional and depend at least upon the type of illumination light beam 12a and the type of image desired, planar or tomographic.

It will also be understood that the gated image intensifier 30 in combination with the light detector 32 is but one arrangement in which images can be generated that are indicative only of early photon portions.

Figure 1A:
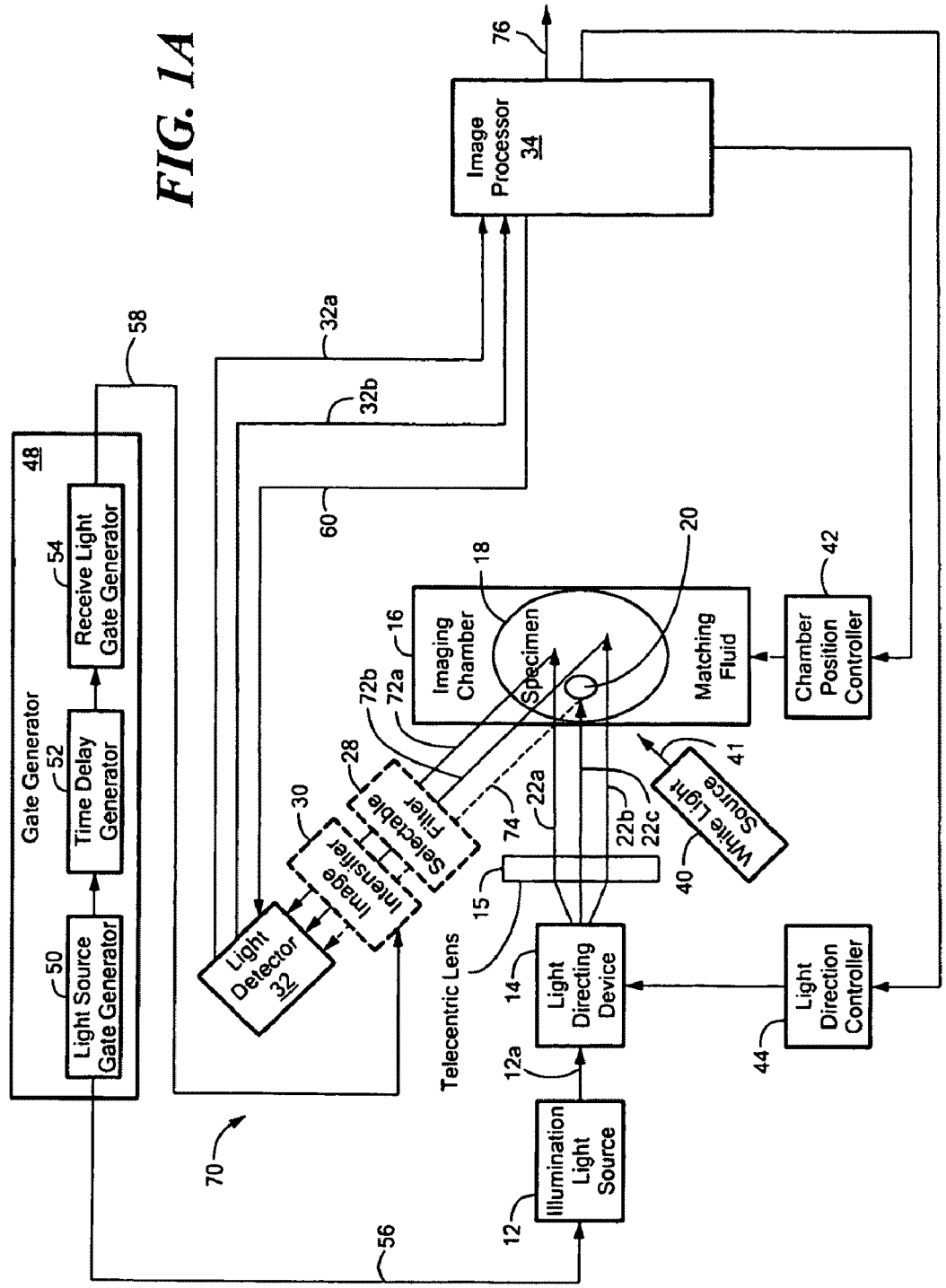
FIG. 1A is a block diagram showing a system for optical tomography having an epi-illumination light source, a light detector, and an image processor.

Referring now to FIG. 1A, in a system 70, in which like elements of FIG. 1 are shown having like reference designations, the selectable filter 28, the gated image intensifier 30, and the light detector 32 are positioned generally on the same side of the specimen 18 as the illumination light source 12 and the light directing device 14. With this particular arrangement, intrinsic light 72a, 72b is received by the light detector 32. Essentially, the illumination light 22a, 22b propagates into the specimen 18 and reflects, or more specifically, scatters, back to the light receiver 32. Fluorescent light 74 is also received by the light detector 32. The system 70 generates a processed fluorescent light image 76.

It should be appreciated that the system 70 provides an epi-illumination imaging system for which illumination light 12a generated by the illumination light source 12 passes into the specimen 18 and is received essentially on the same side of the specimen 18 as the illumination light source 12. In some embodiments, an angle between the light directing device 14 and the image intensifier 30 is approximately ninety degrees. In some other embodiments, an angle between the light directing device 14 and the image intensifier 30 is approximately zero degrees, i.e., they are substantially coaxial.

Figure 1C:
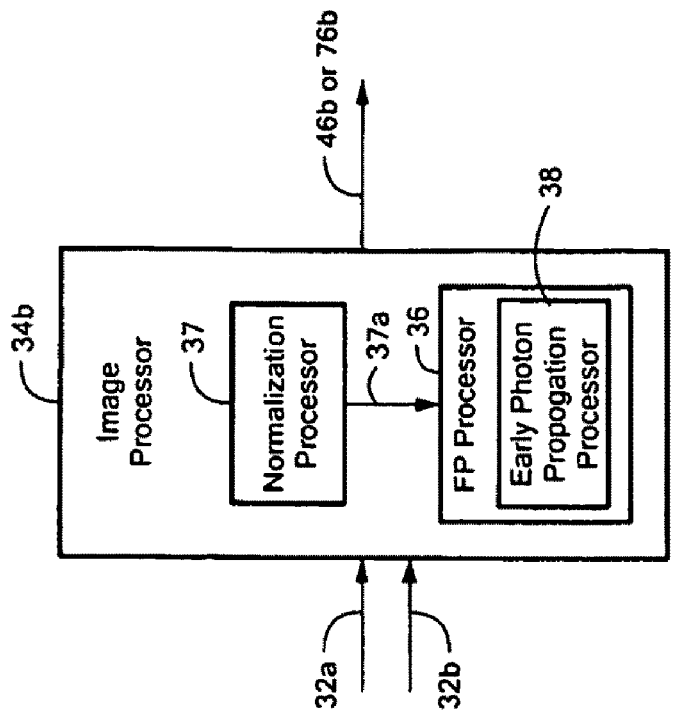
FIG. 1C is a block diagram of another embodiment of the image processor of FIGS. 1 and 1A, which can be used to generate tomographic images having three spatial dimensions.
Figure 1B:
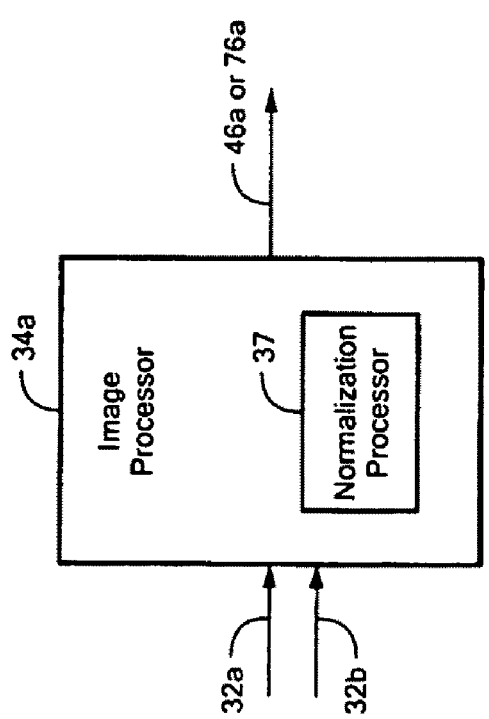
FIG. 1B is a block diagram of one embodiment of the image processor of FIGS. 1 and 1A, which can be used to generate planar images having two spatial dimensions.

Referring now to FIG. 1B, particularly for use in planar imaging, an image processor 34a can include a normalization processor 37. The image processor 34a can be the same as or similar to the image processor 34 of FIGS. 1 and 1A. The normalization processor 37 is operable to combine (e.g., divide) fluorescent light measurements 32a with corresponding intrinsic light measurements 32b, resulting in a processed (or normalized) planar fluorescent light image 46a or 76a (where elements 46 and 76 (see FIGS. 1 and 1A) are indicative of transillumination and epi-illumination images, respectively, and the "a" suffix is representative of a planar image). It will be understood that the combination of the fluorescent light measurements 32a with the intrinsic light measurements 32b results in normalized fluorescent light measurements that can be used to generate a planar processed fluorescent light image 46a or 76a that is substantially corrected for inhomogeneities that may exist in light propagation within the specimen 18. The normalization is described, for example in PCT application PCT/US2005/044651, filed Dec. 8, 2005, published as publication WO 2006/063246 on Jun. 15, 2006, which application is incorporated by reference herein in its entirety.

It will be understood that in order to generate the processed fluorescent light images 46a or 76a, it may be necessary to combine a plurality of fluorescent light measurements 32a and a corresponding plurality of intrinsic light measurements 32b from a corresponding plurality of apparent light source directions 22a-22c in order to achieve the processed fluorescent light images 46a, 76a.

Such normalized images can be acquired at a preferred orientation of the specimen 18. In this orientation the specimen 18 can be mildly restricted between two plates or compressed to conform to a certain thickness, to offer a larger cross-section and to further reduce dynamic range requirements. In some arrangements only a portion of the specimen 18 is imaged. In some arrangements, the specimen 18 may be immersed into a matching fluid to improve the optical image. The matching fluid can be an absorbing or a scattering fluid or both, also improving the dynamic range requirements of the measurements.

Referring now to FIG. 1C, an image processor 34b can include the normalization processor 37 operable to combine (e.g., divide) the fluorescent light measurements 32a with the intrinsic light measurements 32b, resulting in (normalized) fluorescent light measurements 37a. The image processor 34b can be the same as or similar to the image processor 34 of FIGS. 1 and 1A.

Particularly for use in tomographic imaging, the image processor 34b can also include a forward problem (FP) processor 36 coupled to the normalization processor 37. The forward problem processor 36 can simulate a propagation pattern of early photons in a medium (e.g., in the specimen 18). Methods to simulate early photon patterns in the forward problem processor 36 are described more fully below, for example, in conjunction with FIG. 4. Let it suffice here to say that the forward problem processor 36 utilizes a model of light propagation in the specimen 18 (expected light) in combination with the normalized fluorescent light measurements 37a to calculate a distribution of the fluorescent material 20. This calculation is described in more detail below. A tomographic processed fluorescent light image 46b or 76b results, which is substantially corrected for inhomogeneities that may exist in light propagation within the specimen 18.

In some embodiments, solutions to a time-dependent transport equation can allow the light propagation model to predict light propagation for light in the visible wavelength region, having a wavelength of about 400 nm to 700 nm. In other embodiments, solutions to the time-dependent transport equation can allow the model to predict light propagation for light in the near infrared wavelength region, having a wavelength of about 700 nm to 1000 nm. In still other embodiments, solutions to the time-dependent transport equation can allow the model to predict light propagation for light having a wavelength outside of the range of 400 nm-1000 nm. Solutions to the transport equation can be found in Ishimaru, A., "Wave Propagation and Scattering in Random Media", IEEE Press, New York (1999) and Chandrasekhar, S., "Radiative Transfer", Dover Publications, New York (1960).

Figure 2:
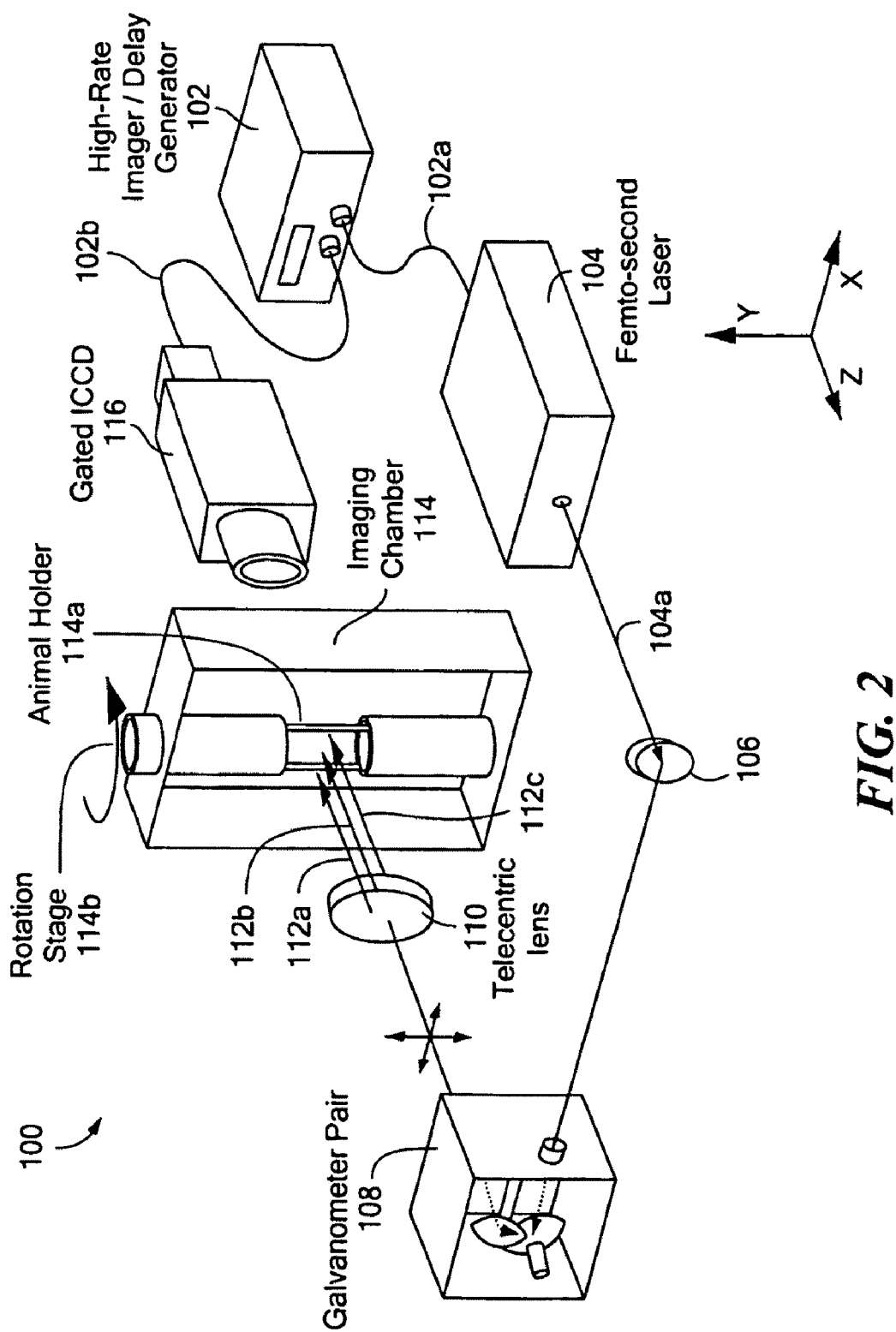
FIG. 2 is a block diagram showing a system for optical tomography having a laser illumination light source, an optical fiber, an optical switch, a light detector in the form of an ICCD camera, and an image processor.

Referring now to FIG. 2, a system 100 for optical imaging using early photons includes a high rate imager/delay generator 102 that provides a transmit gate signal 102a to a femtosecond laser 104. The femto-second laser 104a generates illumination light pulses 104a, which travels to a galvanometer mirror pair 108. The galvanometer mirror pair 108 can generate a plurality of apparent illumination light paths 112a-112c at a variety of positions or angles relative to a specimen (not shown) that can be held in an imaging chamber 114 having an animal holder 114a and a rotation stage 114b. The apparent illumination light 112a-112c can enter the specimen (not shown) resulting in fluorescent light (not shown) and intrinsic light (not shown) exiting the specimen. The intrinsic light and the fluorescent light can be received by an early-photon light detector 116, for example, an image intensifying charge coupled device (ICCD) camera. The early-photon light detector 116 is gated by a receive gate signal 102b generated by the high-rate imager/delay generator 102.

It should be apparent that the high-rate imager/delay generator 102 can be the same as or similar to the gate generator 48 of FIGS. 1 and 1A, the femto-second laser 104 can be the same as or similar to the illumination light source 12 of FIGS. 1 and 1A, the galvanometric pair 108 can be the same as or similar to the light directing device 14 of FIGS. 1 and 1A, the telecentric lens 110 can be the same as or similar to the telecentric lens 15 of FIGS. 1 and 1A, the imaging chamber 114 can be the same a or similar to the imaging chamber 16 of FIGS. 1 and 1A, and the light detector 116 can be the same as or similar to the light detector 32 in combination with the gated image intensifier 30 of FIGS. 1 and 1A.

The system 100 is capable of collecting early photons in a time-gated mode in projections spanning over three hundred sixty degrees. The femto-second laser 104 can be, for example, of a type made by MaiTai, Spectra-Physics, Mountain View, Calif. In one particular arrangement, the femto-second laser 104 generates illumination light pulses (excitation light pulses) at a wavelength of 732 nanometers with an eighty MHz repetition rate, each with a 100 femtosecond pulsewidth. The illumination light 104a can be free-beam coupled (i.e., coupled though the air) to the scanning galvanometer mirror pair 108. Using this arrangement, the laser beam of illumination light 104a can be translated across the imaging chamber 114 with better than 30 microns positional accuracy without significant pulse broadening (<100 fs) when received at the imaging chamber 114.

In some arrangements, the imaging chamber 114 can be immersed in or surrounded by an optical matching fluid. The use of a matching fluid is optional. In some arrangements, a specimen (not shown) within the imaging chamber 114 can be rotated over three hundred sixty degrees in five degree increments, so that single axial slices of the specimen can be scanned using a row of 27 apparent light source positions. Multiple axial slices of the specimen can be scanned at different locations along a length of the specimen in a direction of a y-axis.

Early photons associated with fluorescent light and with intrinsic light (or excitation light) can be captured by the light detector 116, which is some arrangements, can be a high-speed 12-bit gated image intensifier and CCD, for example, as made by LaVision Picostar, Lavision, Germany, with a 200 picosecond imaging gate width and 25 picosecond time step. The light detector 116 can be synchronized to the femto-second laser 104 with an eighty MHz transmit gate signal 102a and a resulting eighty MHz receiver gate signal 102b. Each optical measurement can be captured in accordance with the receive gate signal 102b after a fixed time delay following the laser pulse 104a.

In some arrangements, the receive gate signal 102b can be delayed from the transmit gate signal 102a by approximately 100 picoseconds in accordance with a free-space pulse propagation time of the laser pulse 104a through the illumination light propagation path, including through the imaging chamber 114. This delay can provide an earliest temporal receive window, yielding photon measurements with ~23 dB signal to noise ratio (SNR). This SNR was experimentally found to provide high image reconstruction fidelity. The SNR was calculated using the formula $SNR_1 = 20 \cdot \log_{10}(\mu_1/\sigma_1)$, where $\mu_1$ and $\sigma_1$ are the mean and standard deviation of 100 early photon portion measurements collected using a 100 picosecond receive gate signal 102b, using a diffusive matching fluid, using a 200 millisecond exposure time (corresponding to $1.6 \times 10^7$ laser pulses), and using a single on-axis source-detector pair (i.e., transillumination).

Transmitted early photon measurements can be made both at the wavelength of the illumination light (e.g., excitation light) and at the wavelength of emitted fluorescent light. To this end, a Prosense-750 probe (chromophore) made by Visen Medical of Woburn, Mass. can be used as the fluorescent material. A 10 nanometer bandpass interference filter (not shown) and a long-pass filter (not shown) (e.g., both made by Andover Corporation, Salem, N.H.) with a cut-on wavelength close to or at the wavelength of the fluorescent light can be used to generate intrinsic light measurements and fluorescent light measurements, respectively. The filters correspond to the selectable filter 28 of FIGS. 1 and 1A.

Optical measurements from the gated ICCD camera 116 can be segmented into an array of virtual detectors in post-processing by a computer (e.g., the image processor 34 of FIGS. 1 and 1A). Measured light intensities, measured by virtual detectors disposed directly along positions of the apparent light paths 112a-112c can be used for each projection. Raw fluorescent image measurements can first be normalized as described above in conjunction with FIG. 1B, by combining the raw fluorescent light measurements with the raw intrinsic light measurements, in order to minimize the effects of the inhomogeneities in the optical properties through the specimen (not shown).

As the 100 femtosecond duration laser pulses 104a propagate (e.g., 2.2 cm), through the imaging chamber 114 and specimen (not shown) the pulses broaden drastically to approximately 1.5 nanoseconds as shown below in conjunction with FIG. 3.

To describe the physical propagation of the early photons through the specimen 18 (FIG. 1), a solution or approximate solution to the radiative transport equation can be employed using several possible mathematical models. These can include, but are not limited to, the time-resolved diffusion equation, the cumulant approximation to the transport equation, and hybrid diffusion theory and ballistic photon (unscattered photon) models.

The above-described early photon propagation model can be verified (if needed) by comparing theoretical predictions with experimental measurements of a three-point Green's function through the medium. The Green's function can be derived by step-wise translation of an absorber through an intralipid-filled imaging chamber and measuring the effect on the measured signal intensity of the absorber placed on different locations in the medium. Some comparative results are described below in conjunction with FIG. 4. Alternatively, experimental measurements of early photon propagation as described above can be used and scaled, in the absence of an explicit solution of the transport equation or some of its approximations.

Figure 3:
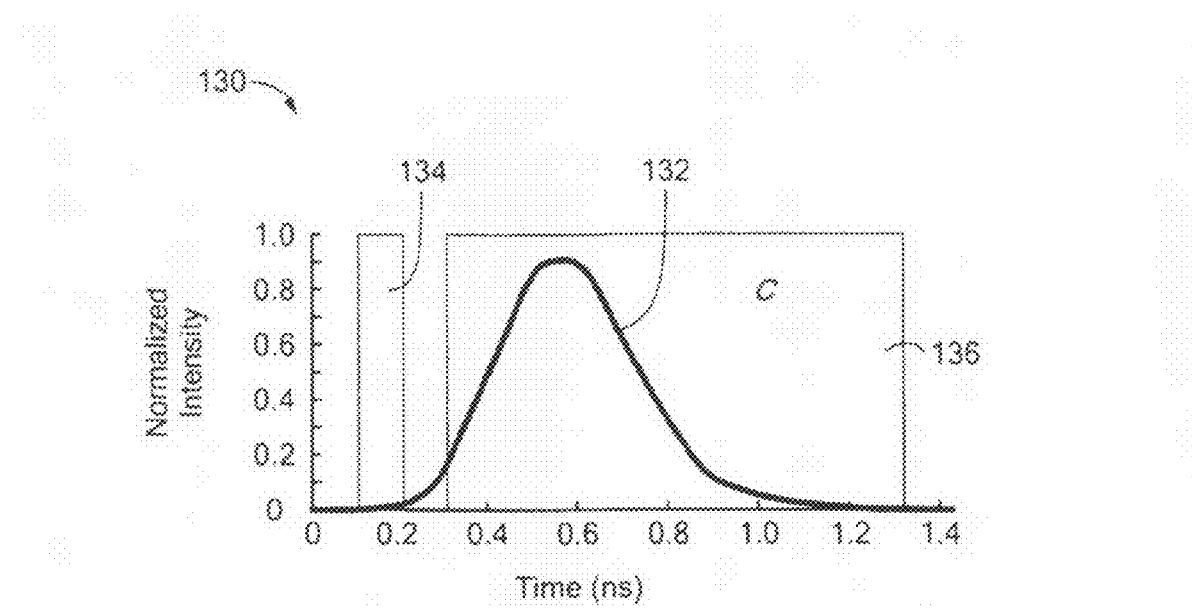
FIG. 3 is a graph showing a time/intensity distribution of light received by a light detector, for example, the light detectors of FIG. 1, 1A, and 2.

Referring now to FIG. 3, graph 130 includes a horizontal axis in unit of time in nanoseconds and a vertical scale showing normalized fluorescent light intensity in arbitrary normalized units. A curve 132 provides an exemplary time distribution of normalized fluorescent light intensities (optical measurements) associated with one or more transmitted illumination light pulses, as received, for example, by the image intensifier 30 of FIGS. 1 and 1A. The term normalized as used in this figure merely refers to the intensity received at a time divided by the maximum intensity measured in the curve 132. It will be understood that the curve 132 is representative of all fluorescent light photons received in conjunction with one (or more) illumination light pulse. The curve 132 can also be representative of received intrinsic light, rather than received fluorescent light.

It will be recognized from the curve 132 that the originally transmitted illumination light pulse of about 100 femtoseconds is broadened to about 1.4 nanoseconds or more when received. Early photons are associated generally with the curve 132 from a time of zero (a first received photon) to a time of about 0.5 nanoseconds (e.g., from zero to the peak). In one particular arrangement, the particular early photons, which are used to generate the images described herein, can extend from a time of about 0.1 nanoseconds to a time of about 0.2 nanoseconds, in a time region 134. However, this early photon portion (i.e., portion of all the photons) is representative of geometries associated with small animals. The exact receive time gate (i.e., early photon portion) can be adjusted in relation to the geometrical specifics (e.g. specimen dimension) and the desired signal to noise ratio in the resulting measurements. As described above, the photons associated with the time region 134 are the photons that propagate nearly directly through a specimen, with few scattering events. The time window 134 corresponds to about ten to twenty percent of the total received photons (i.e., the total time duration of the curve 132). However, as described above, other percentages of the total received photons can be used. The early photon portion can begin at a time of zero, or at a later time as shown.

Figure 4:
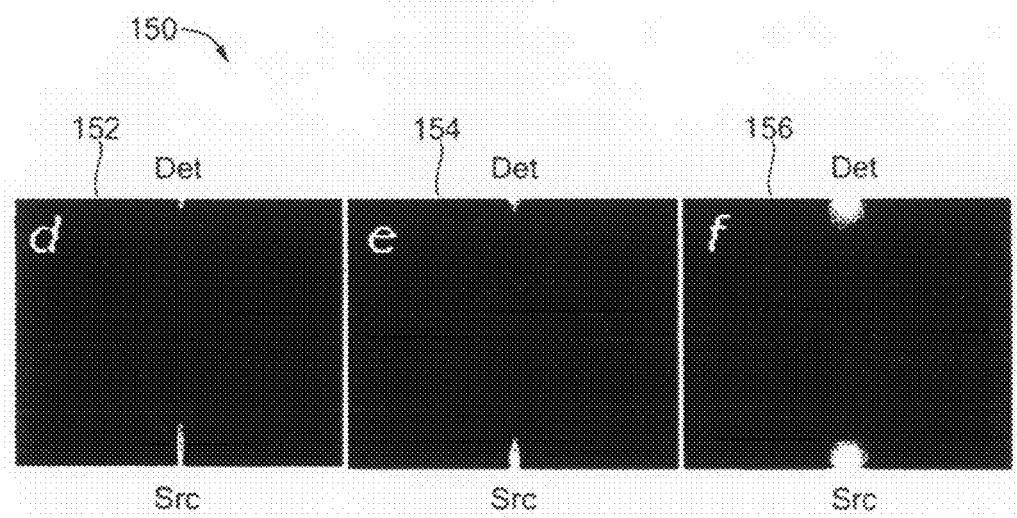
FIG. 4 is a series of three fluorescent light images, each indicative of a different modeled representation of light propagation in a diffuse medium.

Referring now to FIG. 4, an experimentally measured weight function for an early photon portion comparable to the early photon portion within the time window 134 of FIG. 3 is shown in panel 152, wherein the photons travel from a source (Src) to a light detector (Det). A predicted theoretical forward model using the Green's function for the same early photon portion is shown in panel 154. A predicted forward model for a continuous wave (CW) illumination light source is shown in panel 156 for comparison.

A strongly reduced width of the Green's function in panel 154 using the early photon portion versus CW photons in panel 156 is an aspect that can improve resolution of the systems and methods shown and described herein.

Figure 5:
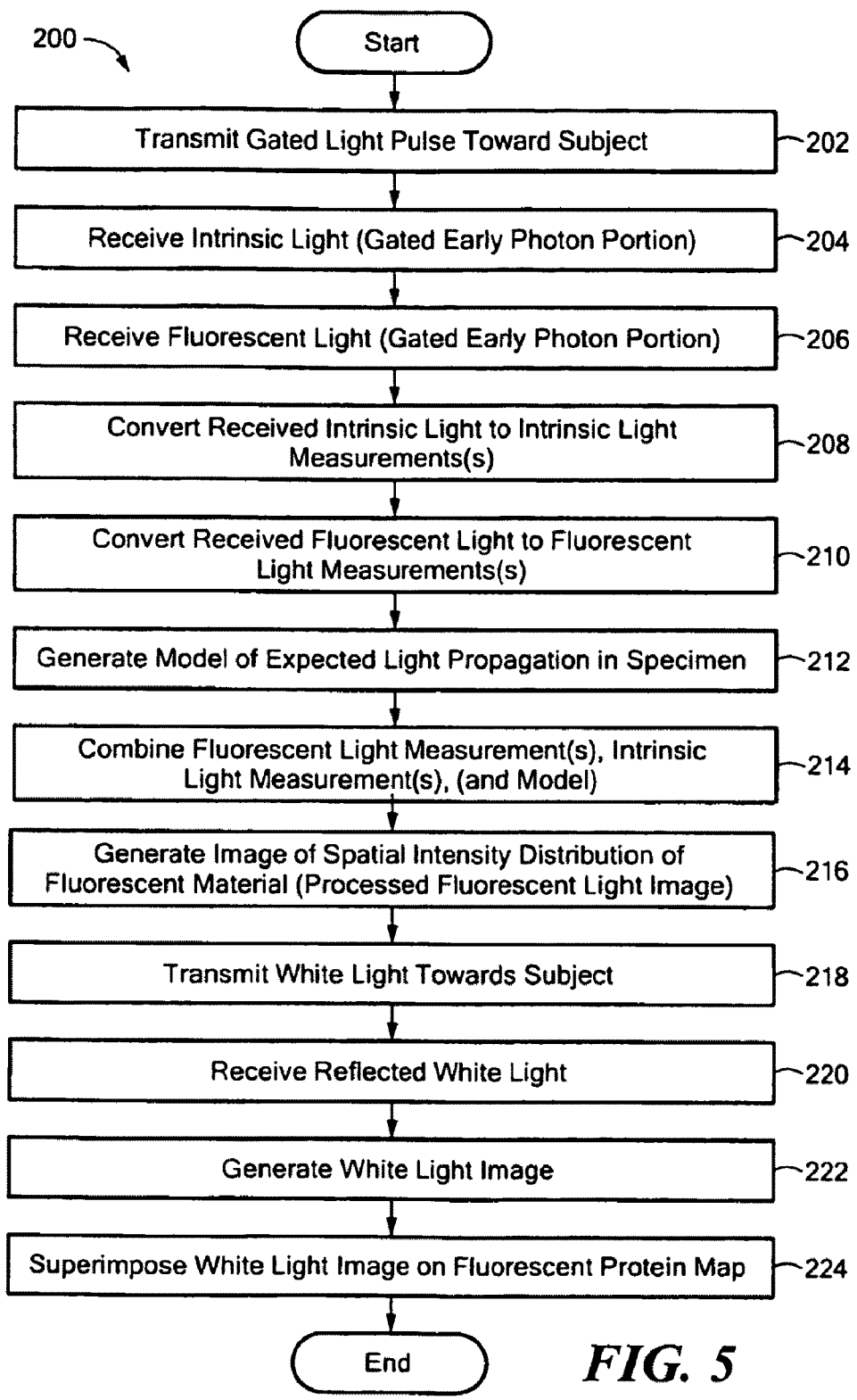
FIG. 5 is a flow chart of a process that can be used in conjunction with the systems of 1, 1A, and 2.

It should be appreciated that FIG. 5 show a flowchart corresponding to the below contemplated technique which would be implemented in computer system 10, 70, 100 (FIGS. 1, 1A, 2). Rectangular elements (typified by element 202 in FIG. 5) herein denoted "processing blocks," represent computer software instructions or groups of instructions.

Alternatively, the processing and decision blocks represent steps performed by functionally equivalent circuits such as a digital signal processor circuit or an application specific integrated circuit (ASIC). The flow diagrams do not depict the syntax of any particular programming language. Rather, the flow diagrams illustrate the functional information one of ordinary skill in the art requires to fabricate circuits or to generate computer software to perform the processing required of the particular apparatus. It should be noted that many routine program elements, such as initialization of loops and variables and the use of temporary variables are not shown. It will be appreciated by those of ordinary skill in the art that unless otherwise indicated herein, the particular sequence of blocks described is illustrative only and can be varied without departing from the spirit of the invention. Thus, unless otherwise stated the blocks described below are unordered meaning that, when possible, the steps can be performed in any convenient or desirable order.

Referring to FIG. 5, a method 200 of optical imaging begins at step 202, where illumination light pulses (e.g., 12a, FIGS. 1 and 1A) including excitation light is generated and transmitted toward a specimen (e.g., 18, FIGS. 1 and 1A). As described above in conjunction with FIG. 1, the illumination light can be provided from a plurality of apparent light sources (e.g., 22a-22c, FIGS. 1 and 1A) corresponding to different positions relative to the specimen or as a broad (planar) light beam, possibly spatially modulated (e.g. differentially attenuated depending upon position upon the specimen 18 (FIG. 1)).

In some embodiments, the plurality of apparent light sources provides illumination light generally simultaneously at the plurality of apparent light sources. In other embodiments, the plurality of apparent light sources provides illumination light sequentially.

At block 204, intrinsic light (e.g., 24a, 24b, FIGS. 1 and 1A), intrinsic light associated with one or more illumination light pulses is received, for example, by the gated image intensifier 30 of FIGS. 1 and 1A. As described above, the intrinsic light corresponds to the illumination light having passed into and out of the specimen. The received intrinsic light is gated to contain only one or more intrinsic light early photon portions by the gated image intensifier 30. In some embodiments, the received intrinsic light results from transillumination light, wherein the light detector and the apparent light sources are essentially on opposite sides of the specimen (see, for example, FIG. 1). In other embodiments the received intrinsic light results from epi-illumination light, wherein the light detector and the apparent light sources are essentially on the same side of the specimen (see, for example, FIG. 1A).

At block 206, fluorescent light associated with associated with the one or more illumination light pulses, are received. The fluorescent light (e.g., 26, FIGS. 1 and 1A) is emitted by fluorescent material (e.g., 20, FIGS. 1 and 1A) within the specimen in response to the intrinsic light. The fluorescent light can be received, for example, by the image intensifier 30 of FIGS. 1 and 1A. The received fluorescent light is gated to contain only one or more fluorescent light early photon portions by the gated image intensifier 30. In some embodiments, the fluorescent light and the intrinsic light are received at the same time, for example, by way of optical filters (e.g., 28, FIGS. 1 and 1A) adapted to separate the fluorescent light from the intrinsic light. In other embodiments, the fluorescent light is received after the excitation light, also by way of an optical filter.

It is to be understood that each measurement made by a light detector (or by a virtual light detector) corresponds to a measurement associated with an illumination light pulse from an illumination light source or with an apparent illumination light source in conjunction with positional knowledge of where the illumination light source is incident upon the tissue. In some embodiments, an optical measurement corresponding to an illumination light source or apparent light source is always collected from a position on the specimen 18 (FIG. 1) that is located in such a way as to provide a shortest path through the specimen 18, between the light source and the light detector.

Correspondingly, in other arrangements associated with tomographic measurements, it is possible to acquire early photons at a plurality of received positions (assuming a single point illumination upon the specimen), by collecting early photons along different assumed paths connecting the single point illumination source to a plurality of light detectors.

The systems and methods described herein provide images of fluorochrome distribution (e.g., concentration) by using the above-described high spatial sampling of photon measurements over multiple projections. High spatial sampling is achieved by utilizing a plurality of closely spaced (in distance) measurements per projection. For example, in some arrangements, for a one centimeter thick object, measurements spatially separated by one millimeter or less in one or two dimensions can be achieved. Coarser spatial sampling tends to degrade imaging performance. Correspondingly, accurate three-dimensional imaging can be obtained by utilizing a plurality of projections, typically more than ten projections and as many as 180 to 360 projections, or more. Projections can be obtained by rotating the optical system (i.e., the light directing device 14, the selectable filter 28, the gatable image intensifier 30, and the light detector 32 of FIG. 1) around the specimen 18 of FIG. 1. In other arrangements, the specimen 18 can be rotated within the optical system as shown in FIGS. 1 and 1A. Rotation of the optical system can be achieved by a rotational device or gantry.

Fluorescent light images can be superimposed with (e.g., overlaid upon) other images provided by x-ray computer-aided tomography CT, positron emission tomography (PET), or single photon emission tomography, utilizing similar geometrical arrangements. In particular, the use of a gantry facilitates the development of hybrid systems for direct co-registration of images from a variety of systems.

At block 208, the received intrinsic light is converted to intrinsic light measurements (e.g., 32b, FIGS. 1 and 1A) by a light detector (e.g., 32, FIGS. 1 and 1A). At block 210, the received fluorescent light is converted to fluorescent light measurements (e.g., 32a, FIGS. 1 and 1A).

At block 212, in particular, where tomographic imaging is being performed, a model is generated to predict light propagation in the specimen. The model can be based on solutions of the transport equation, including the approximate solution utilizing the time-resolved diffusion equation or other physical models. Where planar imaging is being performed, the process of block 212 can be omitted.

The optical model generated at block 212 can be associated with propagation of light in a homogenous medium, i.e. a medium that has no optical heterogeneity. In other embodiments, more advanced models can be also utilized to resolve and then employ information on background optical heterogeneity.

It will become apparent from the discussion below, that light propagation in tissues can be modeled by using the a solution to the so-called "radiative transport equation," or an approximate solution to the radiative transport equation, including, but not limited to, the time-resolved diffusion equation, the cumulant approximation to the transport equation, or hybrid diffusion theory and ballistic photon (unscattered photon) models. Alternatively the experimental determination of early photon propagation in approximate media (e.g., a phantom) having light propagation similar to the specimen being imaged (i.e., the specimen 18 of FIGS. 1 and 1A) can be also utilized. Both the intrinsic light field, which is generated by the illumination light source 12 (FIGS. 1, 1A) upon propagating inside the medium, and the fluorescent light field, which is generated inside the medium due to the fluorescent material 20 (FIGS. 1, 1A), are calculated independently and then used to calculate a normalized field. As described more fully below, the forward problem can be used to provide an image of the fluorescent material 20 inside the specimen 18. The "normalized field" is important because, as described above, it corrects the fluorescent data (i.e., fluorescent light measurements 32a, FIGS. 1a, 1A) using the intrinsic data (i.e., intrinsic light measurements 32b, FIGS. 1a, 1A) so that the specimen 18 can be mathematically approximated as optically homogeneous. This enables accurate computation of the distribution of the fluorescent material 20 even in a highly heterogeneous specimen 18.

A forward model for photon propagation between a source-detector pair, in particular early photons, can include a description of the early-arriving photons including ballistic photons (those photons that are unscattered) and other weakly scattered photons. The normalized field at a measurement time t following the illumination light pulse can be calculated as follows:

$$U^n(r_s, r_d, t) = Q \cdot \frac{1}{G(r_s, r_d, t)} \int \int_0^t G(r, r_d, t-\tau) \cdot \frac{n(r) \cdot v}{D} \cdot G(r_s, r, \tau) \cdot d\tau \cdot d^3r \quad \text{eq. (1)}$$

where Q is a gain factor associated with the different gains of the system at the emission (fluorescent light) and excitation (excitation light) wavelengths, r is a position inside the diffusive medium, $r_s$ and $r_d$ are the source and detector positions of each source-detector pair, respectively, n(r) is a concentration of the fluorescent material in the tissue volume, v is the speed of light in the medium, D is the diffusion coefficient, and G is the Green's function.

Normalization of the forward model with the calculated intrinsic light intensity for light propagating between the source-detector pair (i.e. $G(r_s, r_d, t)$), corresponds to normalization of the fluorescent light measurement with measurements representative of photon propagation in the medium. Normalization of the forward model is necessary for accurate imaging in optically heterogeneous media and for canceling other effects such as boundary interference or spatially dependent gain factors. Normalization significantly improves the accuracy of diffusive fluorescence tomographic imaging systems when imaging objects with strong optical heterogeneity. However this normalization works particularly well with early photons, as both fluorescent light and intrinsic light early photon fields follow approximately the same patterns through the medium.

The Green's function, G, in the above relationship can be given by the photon density calculated using the cumulant solution to the Boltzmann transport equation:

$$G(r, t) = \frac{1}{(4\pi D_{zz}ct)^{1/2}} \frac{1}{4\pi D_{xx}ct} \exp\left[-\frac{(z-R_z(t))^2}{4D_{zz}ct}\right] \times \exp\left[-\frac{(x^2+y^2)}{4D_{xx}ct}\right]\exp(-\mu_a t) \quad (2)$$

where $R_z(t)$ is a moving center of the illumination light source, and $D_{xx}$ and $D_{zz}$ are directional diffusion coefficients defined in detail, for example, in W. Cai, M. Lax and R. Alfano, "Cumulant solution of the elastic Boltzmann transport equation in an infinite uniform medium," Phys. Rev. E. 61, 3871 (2000). The optical properties of the media (i.e. $\mu_s'$ and $\mu_a$) can be pre-determined using fitting of the time-resolved and spatially-resolved photon profiles.

The result can be convolved with a temporal impulse response function of the imaging system, so that the appropriate forward model for a given time-gate can be calculated. In some arrangements described above, the receive time gate used was properly time delayed to occur 100 picoseconds (see, e.g., 134, FIG. 3) after the free-space propagation time of the laser pulse through the imaging chamber.

It should be understood that other physical models of the early photon propagation in the specimen 18 (FIG. 1) can be used to compute the expected light propagation. These include (but are not limited to) the time-resolved diffusion equation and hybrid diffusion theory and ballistic photon (unscattered photon) models. Alternatively, experimental determination of early photon propagation in approximate media (e.g., a phantom) similar to the one being imaged can be also utilized. Finally, crude approximations of forward propagation of pencil beams, i.e. assuming un-scattered photon fields, can also be utilized to form tomographic images, but are expected to generate worse imaging performance compared to the other models described above.

At block 214, in particular for tomographic imaging, the intrinsic light measurements generated at block 208, corresponding fluorescent light measurements generated at block 210, and the light propagation model generated at block 212 are combined, for example, in the above-described "forward model." Where the specimen has internal fluorescent material and is therefore not internally homogeneous, the combining at block 214 can generate an "image problem" or "forward model" of the form: measurements=(forward model)×(unknown distribution), where the measurements are provided at blocks 208-210 by the light detector 32 (FIG. 1) and the forward model is provided at block 212 by the image processor 34 (FIG. 1), generally in accordance with equations above. The unknown distribution corresponds to the distribution of fluorescent light emitted by the fluorescent material within the specimen.

Mathematically, the forward model is described as the matrix equation y=W·x, where y are the measurements, W are the theoretical predictions given by the physical model described above, and x is the fluorescent material bio-distribution. The image processor 34 can solve for the unknown distribution in order to establish physical positions and characteristics of the fluorescent material (20, FIGS. 1 and 1A) in the specimen (18, FIG. 1 an 1A).

At block 216, an image of the spatial distribution (e.g., concentration) of fluorescent material in the specimen, i.e., a processed fluorescent light image (46 or 76, FIGS. 1, 1A, respectively) is generated. Image generation can be performed by direct inversion of the matrix, W, after its singular value decomposition (SVD) with Tikhonov regularization. In other arrangements, the algebraic reconstruction technique (ART) was also found adequate to produce accurate images. The image generation process of block 216 requires approximately fifteen seconds on a 2.8 MHz Pentium 4 personal computer using the Matlab software package (The Mathworks Inc, Natick, Mass.) and custom written software. Other inversion methods of the matrix W can also be utilized.

Alternatively, at block 214, in particular for planar imaging, the intrinsic light measurements generated at block 208, and the fluorescent light measurements generated at block 210 can be combined to provide a normalized image, without use of a forward model, as described above in conjunction with FIG. 1B. In this case, the resulting image has two spatial dimensions rather than three spatial dimensions.

For a tomographic image, in generating the image representative of the distribution (e.g., concentration) of the fluorescent material 20 (FIGS. 1, 1A), the volume of interest can be segmented into axial (horizontal) layers (e.g., 21 layers) each containing a number (e.g., 651) of voxels or sagital or coronal layers.

The volume of interest can be segmented in a number of voxels in three dimensions. These can be seen as horizontal, vertical, or transverse layers, resembling cubes stacked next to each other in three dimensions. The voxel size is selected based upon the dimension of the field of view and the number of segmentations. Each of the voxels has an unknown amount of fluorescent material and an unknown attenuation.

It may be desirable, in some planar and in some tomographic arrangements, to optionally superimpose a white light image of the specimen onto the image of the distribution of fluorescent material in the specimen, in order to give enhanced understandability of the image. To this end, the specimen can be illuminated by a white light source at block 218 and a white light can be received at block 220 and a white light image can be generated at block 222.

The white light image generated at block 222 can be superimposed at block 224 with the image of the distribution of fluorescent material in the specimen generated at block 216. To this end, in one particular embodiment, the white light image is registered or aligned with the image of distribution of fluorescent material in the specimen generated at block 216.

In order to align the white light image with the image of the distribution of fluorescent material in the specimen, an image of the apparent light sources can be made, for example, through a phantom, to allow the apparent light source coordinates to be determined. This procedure improves the co-registration of a white light image that can be superimposed upon tomographic images, reducing relative positional errors.

In other arrangements, it may be desirable to superimpose another type of image upon the image of the distribution of fluorescent material in the specimen. For example, an x-ray computer aided-tomography (CT) image, a magnetic resonance image (MRI), or a positron emission tomography (PET) image can be superimposed with the image of the distribution of fluorescent material in the specimen.

Figures 6, 6A:
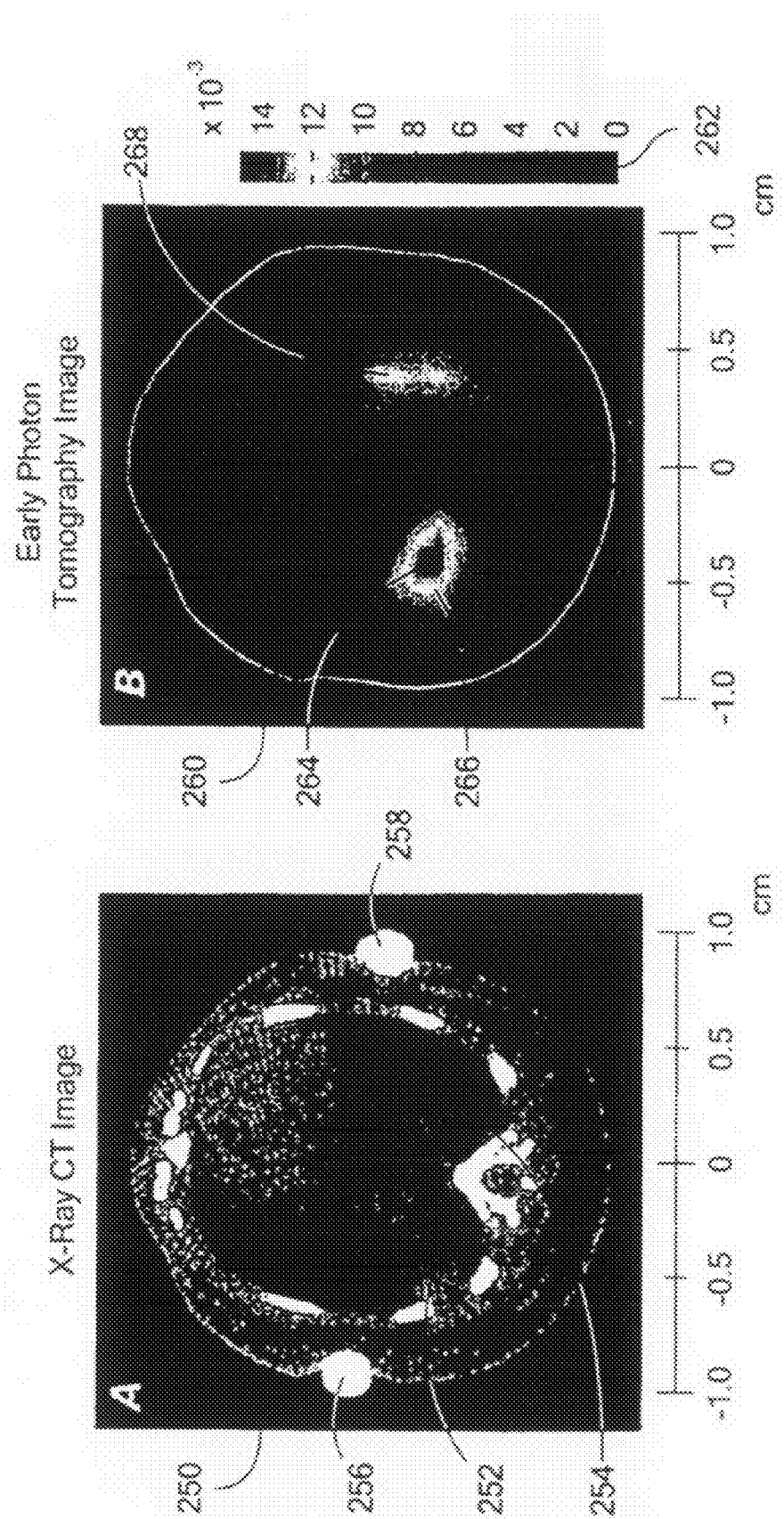
FIG. 6 is a conventional x-ray computer aided tomography (CT) image of tissue of a small animal having a tumor.
FIG. 6A is a processed fluorescent light image of the tissue of the small animal of FIG. 6, wherein a fluorescent material that tends to concentrate in tumors has been infused into the tissue.

Referring now to FIG. 6, an image 250 of tissue of a small animal is a conventional x-ray CT image. In the image 250, a tumor 252 and also a pre-cancerous region 254, cannot be readily identified. Features 256, 258 correspond to bars seen in the animal holder 114a of FIG. 2.

Referring now to FIG. 6A, an image 260 of the tissue of the small animal of FIG. 6 is a processed fluorescent light image in accordance with the processed fluorescent light image 46 of FIG. 1, which is generated in the above described transillumination mode. A fluorescent probe or marker, which tends to concentrate in tumors, has been infused into the tissue prior to generation of the image 260. A color scale (reproduced in grey scale) provides colors associated with concentrations of the fluorochrome in arbitrary molar units. It will be understood that the image 260, which includes color regions (reproduced in grey scale) is indicative of an image of the distribution of fluorescent material in the tissue.

The image 260 includes a region 264 having a color (shown in grey scale) indicative of a fluorochrome concentration of about $14 \times 10^{-3}$ (arbitrary units), and two regions 266, 268 having a color (shown in grey scale) indicative of a lesser fluorochrome concentration of about $12 \times 10^{-3}$ (arbitrary units). Other color regions in the image 260 are not readily visible in the grey scale reproduction, but are indicative of lower fluorochrome concentrations. It will be understood that the regions 264, 266 correspond to the tumor 252 of FIG. 6, and the region 268 corresponds to the pre-cancerous region 254 of FIG. 6. The regions 264, 266, 268 are readily visible in color, and even in this grey scale reproduction.

Since the image 260 may be difficult to spatially interpret, not having a reference tissue boundary, it may be desirable, as described above, to superimpose another image upon the processed fluorescent light image 260.

Figure 6B:
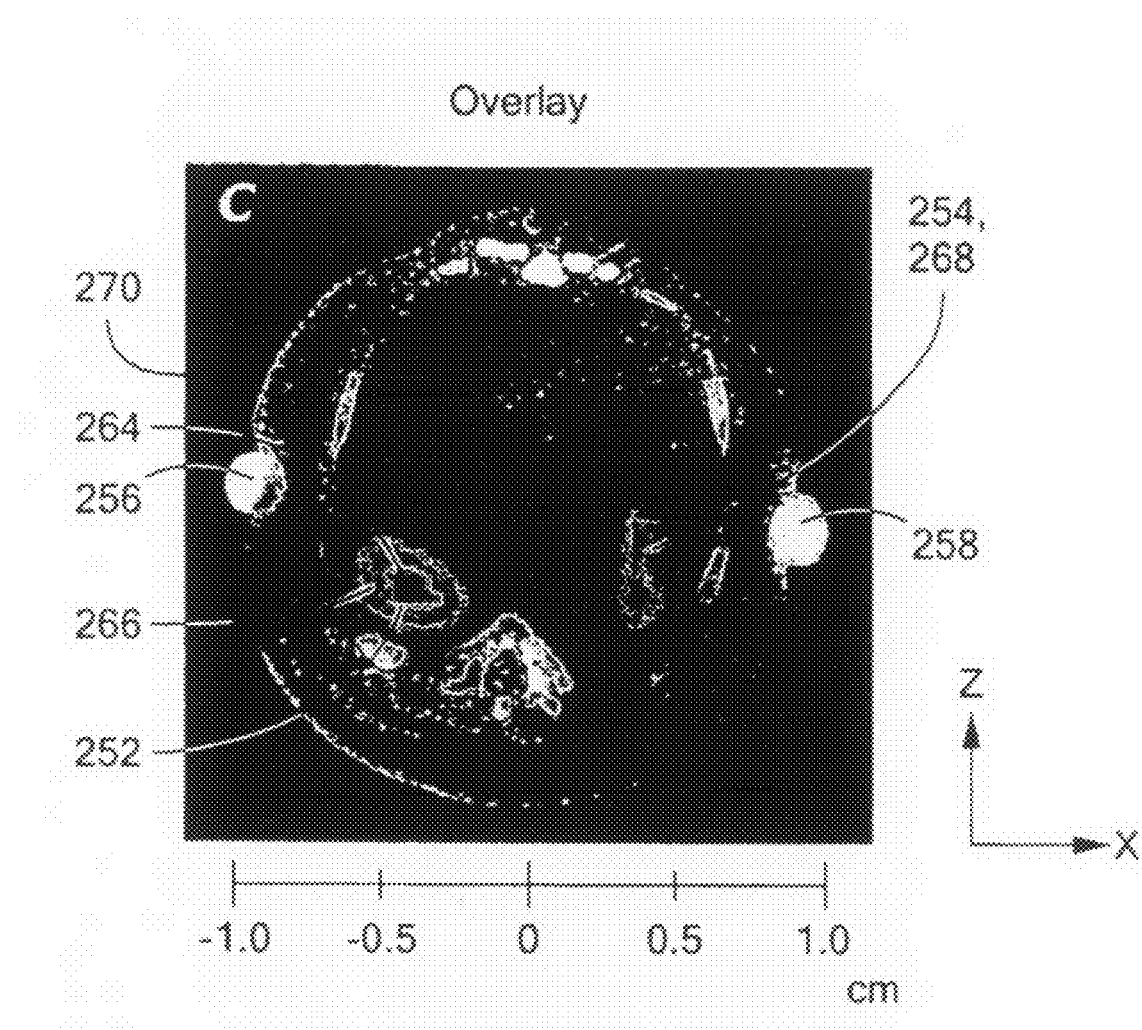
FIG. 6B is the processed fluorescent light image of FIG. 6A superimposed with the CT image of FIG. 6.

Referring now to FIG. 6B, in which like elements of FIGS. 6 and 6A are shown having like reference designations, an image 270 is an overlay of the CT image 250 of FIG. 6 with the processed fluorescent light image 260 of FIG. 6A. In the superimposed image 270, the tumor 252 and the pre-cancerous region 254 are readily visible as are their positions within the tissue.

The methods described herein may include selectively imaging a subject containing two or more imaging probes simultaneously, wherein two or more imaging probes are administered to a subject, either at the same time or sequentially. The methods therefore allow the recording of multiple biological processes, functions or targets.

The methods of the invention can be used to determine a number of indicia, including tracking the localization of the imaging probes in the subject over time or assessing changes or alterations in the metabolism and/or excretion of the imaging probes in the subject over time. The methods can also be used to follow therapy for such diseases by imaging molecular events and biological pathways modulated by such therapy, including but not limited to determining efficacy, optimal timing, optimal dosing levels (including for individual patients or test subjects), and synergistic effects of combinations of therapy.

The invention can be used to help a physician or surgeon to identify and characterize areas of disease, such as arthritis, cancers, or vulnerable or unstable plaque, to distinguish diseased and normal tissue, such as detecting tumor margins that are difficult to detect.

The methods of the invention can also be used in the detection, characterization and/or determination of the localization of a disease, especially early disease, the severity of a disease or a disease-associated condition, the staging of a disease, and monitoring and guiding various therapeutic interventions, such as surgical procedures, and monitoring drug therapy and delivery, including cell based therapies. The methods of the invention can also be used in prognosis of a disease or disease condition. Examples of such disease or disease conditions include inflammation (e.g., inflammation caused by arthritis, for example, rheumatoid arthritis), cancer (e.g., colorectal, ovarian, lung, breast, prostate, cervical, skin, brain, gastrointestinal, mouth, esophageal, bone), cardiovascular disease (e.g., atherosclerosis and inflammatory conditions of blood vessels, ischemia, stroke, thrombosis), dermatologic disease (e.g., Kaposi's Sarcoma, psoriasis), ophthalmic disease (e.g., macular degeneration, diabetic retinopathy), infectious disease (e.g., bacterial, viral, fungal and parasitic infections, including Acquired Immunodeficiency Syndrome), immunologic disease (e.g., an autoimmune disorder, lymphoma, multiple sclerosis, rheumatoid arthritis, diabetes mellitus), central nervous system disease (e.g., a neurodegenerative disease, such as Parkinson's disease or Alzheimer's disease), inherited diseases, metabolic diseases, environmental diseases (e.g., lead, mercury and radioactive poisoning, skin cancer), and bone-related disease (e.g., osteoporosis, primary and metastatic bone tumors, osteoarthritis). The methods of the invention can therefore be used, for example, to determine the presence of tumor cells and localization of tumor cells, the presence and localization of inflammation, including the presence of activated macrophages, for instance in atherosclerosis or arthritis, the presence and localization of vascular disease including areas at risk for acute occlusion (i.e., vulnerable plaques) in coronary and peripheral arteries, regions of expanding aneurysms, unstable plaque in carotid arteries, and ischemic areas. The methods and compositions of the invention can also be used in identification and evaluation of cell death, injury, apoptosis, necrosis, hypoxia and angiogenesis.

In certain embodiments, an x-ray computed tomography (CT) system is used in combination with the fluorescence molecular tomography (FMT) methods and systems described herein that make use of early arriving photon detection. An x-ray computed tomography system generates a surface model (e.g., a three-dimensional mathematical description) of at least a portion of the surface of the subject, with such surface model providing the optical tomography reconstruction algorithm with the boundary conditions necessary for its computation. The combined imaging system further includes a surface model processor coupled to the optical surface-capture system and/or to the x-ray tomographic system to provide one or more surface models associated with the surface of the subject. A solution processor coupled to the data collection systems and the model processor provides a combined optical and x-ray tomographic image of the object in response to the one or more signals and to the one or more surface models described more fully in WO 2004/072906 and WO 2003/102558. More details regarding the combined x-ray computed tomography (CT) and fluorescence molecular tomography (FMT) system and methods, to which features of the early-arriving photon detection systems and methods discussed herein may be applied, are described in International Publication No. WO2007/111669, published Oct. 4, 2007, International Application No. PCT/US2006/048785, the text of which is incorporated herein by reference in its entirety.

For example, methods of in vivo imaging with a combined CT/FMT system may include administering to a subject an optical imaging probe; allowing time for the optical imaging probe to distribute in the subject; positioning the subject in a combined imaging system; collecting the x-ray and optical tomographic data sets sequentially or simultaneously; and displaying the tomographic datasets as x-ray and optical images either alone or fused. These steps can also be repeated at predetermined intervals thereby allowing for the evaluation of the subject over time. The subject may be a vertebrate animal, for example, a mammal, including a human.

All references cited herein are hereby incorporated herein by reference in their entirety.

Having described preferred embodiments of the invention, it will now become apparent to one of ordinary skill in the art that other embodiments incorporating their concepts may be used. It is felt therefore that these embodiments should not be limited to disclosed embodiments, but rather should be limited only by the spirit and scope of the appended claims.

What is claimed is:

1. A system for optical imaging, comprising:
    a light source configured to project illumination light comprising one or more illumination light pulses into a specimen having a fluorescent material therein, wherein said illumination light comprises excitation light that becomes intrinsic light within said specimen and excites said fluorescent material, thereby producing fluorescent light, wherein at least a portion of said fluorescent light and said intrinsic light exit said specimen;
    an early-photon light detector configured to detect one or more fluorescent light early photon portions associated with said exiting fluorescent light and one or more intrinsic light early photon portions associated with said exiting intrinsic light, wherein each fluorescent light early photon portion is a portion of said fluorescent light less than all of said fluorescent light associated with a corresponding illumination light pulse and wherein each intrinsic light early photon portion is a portion of said intrinsic light less than all of said intrinsic light associated with a corresponding illumination light pulse, wherein said early-photon light detector is configured to generate a fluorescent light measurement that is a time-dependent function associated with said one or more fluorescent light early photon portions and is configured to generate an intrinsic measurement that is a time-dependent function associated with said one or more intrinsic light early photon portions; and
    an image processor configured to combine said fluorescent light measurement and said intrinsic light measurement in a time-dependent combination to generate a fluorescent light image from said processed data, said fluorescent light image representative of a spatial distribution of said fluorescent material in at least two dimensions.

2. The system of claim 1, wherein said light source is spatially separated from said specimen so that said illumination light travels through air to said specimen.

3. The system of claim 1, wherein said early-photon light detector is spatially separated from said specimen so that said detected fluorescent light early photon portions and said detected intrinsic light early photon portions travel through air.

4. The system of claim 1, wherein said image processor is configured to provide a normalized fluorescent light measurement representative of at least one of said detected fluorescent light early photon portions using said fluorescent light measurement and said intrinsic light measurement, thereby adjusting for inhomogeneity of light propagation within said specimen.

5. The system of claim 4, wherein said image processor is configured to provide a tomographic fluorescent light image representative of said spatial distribution of said fluorescent material in three physical dimensions using a model of early-photon propagation in a diffuse medium and using said normalized fluorescent light measurement, thereby adjusting for inhomogeneity of light propagation within said specimen.

6. The system of claim 1, wherein said image processor is configured to generate a normalized fluorescent light image representative of said spatial distribution of said fluorescent material in at least two physical dimensions by generating a raw fluorescent light image using said fluorescent light measurement, generating a raw intrinsic light image using said intrinsic light measurement, and combining said raw intrinsic light image and said raw fluorescent light image.

7. The system of claim 6, wherein said image processor is configured to provide a tomographic fluorescent light image representative of said spatial distribution of said fluorescent material in three physical dimensions using a model of early-photon propagation in a diffuse medium and using said normalized fluorescent light measurement, thereby adjusting for inhomogeneity of light propagation within said specimen.

8. The system of claim 1, wherein said light source is configured to direct said illumination light into said specimen at multiple locations, resulting in a plurality of projections.

9. The system of claim 8, wherein said light source is configured to transilluminate at least a portion of said specimen.

10. The system of claim 8, wherein said light source is configured to epi-illuminate said specimen.

11. The system of claim 8, wherein said early-photon light detector is configured to detect said one or more fluorescent light early photon portions and said one or more intrinsic light early photon portions at each of said plurality of projections.

12. The system of claim 8, wherein said early-photon light detector is configured to move about said specimen to a plurality of positions and to receive said one or more fluorescent light early photon portions and said one or more intrinsic light early photon portions at a plurality of positions.

13. The system of claim 8, further comprising a movable stage configured to hold said specimen and configured to move said specimen to a plurality of positions and to receive said one or more fluorescent light early photon portions and said one or more intrinsic light early photon portions at a plurality of positions, resulting in a plurality of projections.

14. The system of claim 1, further comprising one or more light filters disposed between said specimen and said early-photon light detector, said one or more light filters configured to transmit said one or more fluorescent light early photon portions and to block said one or more intrinsic light early photon portions at a first time and configured to block said one or more fluorescent light early photon portions and to transmit said one or more intrinsic light early photon portions at a second time.

15. The system of claim 1, further comprising:
    a first light filter disposed between said specimen and said early-photon light detector and configured to transmit said one or more fluorescent light early photon portions and to block said one or more intrinsic light early photon portions; and
    a second light filter disposed between said specimen and said early-photon light detector and configured to block said one or more fluorescent light early photon portions and to transmit said one or more intrinsic light early photon portions.

16. The system of claim 1, wherein said fluorescent light early photon portion for a given illumination light pulse has an associated time extent, wherein said intrinsic light early photon portion for said given illumination light pulse has an associated time extent, and wherein said fluorescent light early photon portion time extent is no greater than about twenty percent of said time extent corresponding to all fluorescent light photons associated with said given illumination light pulse, and said intrinsic light early photon portion time extent is no greater than about twenty percent of said time extent corresponding to all intrinsic light photons associated with said given illumination light pulse.

17. The system of claim 1, wherein said fluorescent light early photon portion for a given illumination light pulse has an associated time extent, wherein said intrinsic light early photo portion for said given illumination light pulse has an associated time extent, and wherein said fluorescent light early photon portion time extent is no greater than about fifty percent of said time extent corresponding to all fluorescent light photons associated with said given illumination light pulse, and said intrinsic light early photon portion time extent is no great than about fifty percent of said time extent corresponding to all intrinsic light photons associated with said given illumination light pulse.

18. The system of any one of claims 16-17, wherein said fluorescent light early photon time extent is no greater than about 200 picoseconds and said intrinsic light early photon time extent is no greater than about 200 picoseconds.

19. The system of claim 1, wherein a spatial extent of said one or more illumination light pulses is less than a dimension of said specimen.

20. The system of claim 1, wherein said fluorescent light image is generated in accordance with a plurality of fluorescent light early photon portions and a plurality of intrinsic light early photon portions corresponding to a plurality of illumination light pulses.

21. The system of claim 1, wherein said specimen is diffuse to propagation of said intrinsic light and said fluorescent light.

22. The system of claim 1, wherein said illumination light has a wavelength from about 400 nm to about 1000 nm.

23. The system of claim 22, wherein said illumination light has a wavelength from about 400 nm to about 700 nm.

24. The system of claim 22, wherein said illumination light has a wavelength from about 700 nm to about 1000 nm.

25. The system of claim 1, wherein said fluorescent light has a wavelength from about 400 nm to about 1000 nm.

26. The system of claim 25, wherein said fluorescent light has a wavelength from about 400 nm to about 700 nm.

27. The system of claim 25, wherein said fluorescent light has a wavelength from about 700 nm to about 1000 nm.

28. The system of claim 1, wherein said fluorescent material comprises a fluorescent protein.

29. The system of claim 1, wherein said fluorescent material comprises a fluorescent probe.

30. The system of claim 1, further comprising a gate generator coupled to said early-photon light detector and configured to generate a receive gate signal in accordance with said one or more fluorescent light early photon portions and in accordance with said one or more intrinsic light early photon portions detected by said early-photon light detector.

31. The system of claim 30, wherein said gate generator is further coupled to said light source and further configured to generate a transmit gate signal to control a duration of said one or more illumination light pulses.

32. The system of claim 28, wherein said gate generator further comprises a time delay module configured to generate a time delay signal to provide a time delay between said transmit gate signal and said receive gate signal.

33. The system of claim 32, wherein said time delay module provides different time delays for said one or more fluorescent light early photon portions detected by said early-photon light detector than for said one or more intrinsic light early photon portions detected by said early-photon light detector.

34. The system of claim 1, wherein said early-photon light detector comprises a gatable image intensifier.

35. The system of claim 1, wherein said early-photon detector comprises a time-to-amplitude converter.

36. The system of claim 1, wherein said specimen is a mammal.

37. The system of claim 36, wherein said mammal is a mouse.

38. The system of claim 1, wherein said fluorescent material comprises a substance endogenous to said specimen.

39. The system of claim 1, wherein said fluorescent material comprises a substance administered to said specimen prior to said optical imaging.

40. The system of claim 1, wherein the time-dependent combination comprises a convolution of said fluorescent light measurement with said intrinsic light measurement.

41. The system of claim 40, wherein the time-dependent combination further comprises a division of the convolution by the intrinsic light measurement.

42. A method of providing a representation of a spatial distribution of fluorescent material within a specimen, the method comprising:
  (a) directing one or more pulses of illumination light comprising excitation ; light into a specimen at one or more locations, said excitation light becoming intrinsic light within said specimen and said intrinsic light exiting said specimen;
  (b) detecting one or more intrinsic light early photon portions exiting said specimen, wherein each intrinsic light early photon portion is a respective portion of said intrinsic light less than all of said intrinsic light associated with a respective illumination light pulse;
  (c) detecting one or more fluorescent light early photon portions exiting said specimen, wherein each fluorescent light early photon portion is a respective portion of fluorescent light produced from fluorescent material within said specimen as a result of a respective illumination light pulse, and wherein each fluorescent light early photon portion is less than all of said fluorescent light produced from said fluorescent material within said specimen as a result of a respective illumination light pulse;
  (d) generating a fluorescent light measurement that is a time-dependent function associated with said one or more fluorescent light early photon portions;
  (e) generating an intrinsic light measurement that is a time-dependent function associated with said one or more intrinsic light early photon portions; and
  (f) combining said fluorescent light measurement and said intrinsic light measurement in a time-dependent combination to generate a fluorescent light image representation of a spatial distribution of said fluorescent material within said specimen.

43. The method of claim 42, wherein said one or more pulses of illumination light comprise continuous wave CW pulses comprising the excitation light, the method further comprising:
  directing the continuous wave (CW) excitation light into said specimen;
  detecting CW fluorescent light exiting said specimen said CW fluorescent light produced a result of said CW excitation light; and
  generating said fluorescent light measurement in accordance with said CW fluorescent light.

44. The method of claim 43, further comprising:
detecting CW intrinsic light exiting said specimen; and
generating said fluorescent light measurement in accordance with said CW fluorescent light and generating said intrinsic light measurement in accordance with said CW intrinsic light.

45. The method of claim 42, wherein said one or more pulses of illumination light comprise frequency-modulated (FM) pulses comprising excitation light, the method further comprising:
directing the frequency-modulated (FM) excitation light into said specimen; and
detecting FM fluorescent light exiting said specimen, said FM fluorescent light produced as a result of said FM excitation light; and
generating said fluorescent light measurement in accordance with said FM fluorescent light.

46. The method of claim 45, further comprising:
detecting FM intrinsic light exiting said specimen corresponding to said FM excitation light; and
generating said fluorescent light measurement in accordance with said FM fluorescent light and generating said intrinsic light measurement in accordance with said FM intrinsic light.

47. The method of claim 42, wherein said combining further comprises generating a tomographic representation of a three-dimensional distribution of said fluorescent material within said specimen.

48. The method of claim 42, wherein said fluorescent light early photon portion for a given illumination light pulse has an associated time extent, wherein said intrinsic light early photon portion for said given illumination light pusle has an associated time extent, and wherein said fluorescent light early photon portion time extent is no greater than about twenty percent of said time extent corresponding to all fluorescent light photons associated with said given illumination light pulse, and said intrinsic light early photon portion time extent is no greater than about twenty percent of said time extent corresponding to all intrinsic light photons associated with said given illumination light pulse.

49. The method of claim 42, wherein said fluorescent light early photon portion for a given illumination light pulse has an associated time extent, wherein said intrinsic light early photon portion for said given illumination light pulse has an associated time extent, and wherein said fluorescent light early photon portion time extent is no greater than about fifty percent of said time extent corresponding to all fluorescent light photons associated with said given illumination light pulse, and said intrinsic light early photon portion time extent is no great than about fifty percent of said time extent corresponding to all intrinsic light photons associated with said given illumination light pulse.

50. The method of claim 42, wherein said fluorescent light early photon portion for a given illumination light use has an associated time extent, wherein said intrinsic light early photon portion for said given illumination light rinse has an associated time extent, and wherein said fluorescent light early photon time extent is no greater than about 200 picoseconds and said intrinsic light early photon time extent is no greater than about 200 picoseconds.

51. The method of claim 42, wherein said illumination light has a wavelength from about 400 nm to about 1000 nm.

52. The method of claim 51, wherein said illumination light has a wavelength from about 400 nm to about 700 nm.

53. The method of claim 51, wherein said illumination light has a wavelength from about 700 nm to about 1000 nm.

54. The method of claim 42, wherein said fluorescent light has a wavelength from about 400 nm to about 1000 nm.

55. The method of claim 54, wherein said fluorescent light has a wavelength from about 400 nm to about 700 nm.

56. The method of claim 54, wherein said fluorescent light has a wavelength from about 700 nm to about 1000 nm.

57. The method of claim 42, wherein said fluorescent material comprises a fluorescent protein.

58. The method of claim 42, wherein said fluorescent material comprises a fluorescent probe.

59. The method of claim 42, wherein said specimen is a mammal.

60. The method of claim 59, wherein said mammal is a mouse.

61. The method of claim 42, wherein said fluorescent material comprises a substance endogenous to said specimen.

62. The method of claim 42, wherein said fluorescent material comprises a substance administered to said specimen prior to said optical imaging.

63. The method of claim 42, wherein the combining comprises generating a convolution of said fluorescent light measurement with said intrinsic light measurement.

64. The method of claim 63, wherein the combining further comprises dividing the convolution by the intrinsic light measurement.

* * * * *

UNITED STATES PATENT AND TRADEMARK OFFICE
CERTIFICATE OF CORRECTION

PATENT NO. : 8,314,406 B2  
APPLICATION NO. : 12/594351  
DATED : November 20, 2012  
INVENTOR(S) : Vasilis Ntziachristos et al.

Page 1 of 1

It is certified that error appears in the above-identified patent and that said Letters Patent is hereby corrected as shown below:

In the Specification

Column 24, line 35 delete "$SNR_1 = 20 \cdot \log_{10}(\mu_1/\sigma_1)$," and replace with --$SNR_1 = -20 \cdot \log_{10}(\mu_1/\sigma_1)$--.

In the Claims

Claim 42, Column 36, line 24 delete "excitation; light" and replace with --excitation light--.

Signed and Sealed this  
Twenty-third Day of September, 2014

Michelle K. Lee  
*Deputy Director of the United States Patent and Trademark Office*